United States Patent [19]

LaBell et al.

[11] Patent Number: 5,438,141

[45] Date of Patent: Aug. 1, 1995

[54] HETEROARYL AND HALOARYL QUINOLINE DERIVATIVES OF CYCLOPROPANEACETIC ACID AS LEUKOTRIENE ANTAGONISTS

[75] Inventors: Marc LaBell, Ile Perrot; Yves LeBlanc, Kirkland; Michel Belley, Pierrefonds; Erich L. Grimm, Baie d'Urfe; Daniel Guay, Notre Dame De L'Ile Perrot, all of Canada; Yi B. Xiang, Lexington, Mass.

[73] Assignee: Merck Frosst Canada, Inc., Kirkland, Canada

[21] Appl. No.: 65,734

[22] Filed: May 21, 1993

[51] Int. Cl.$^6$ .............. C07D 401/06; C07D 215/16; A61K 31/41; A61K 31/47
[52] U.S. Cl. .................. 546/176; 546/177; 546/174; 514/311
[58] Field of Search ........... 546/176, 177, 174; 514/311

[56] References Cited

FOREIGN PATENT DOCUMENTS 0315399 5/1989 European Pat. Off. .
0348155 12/1989 European Pat. Off. .
0349062 1/1990 European Pat. Off. .
0399818 11/1990 European Pat. Off. .
0480708 4/1992 European Pat. Off. .
0480716 4/1992 European Pat. Off. .
0480717 4/1992 European Pat. Off. .

Primary Examiner—David B. Springer
Attorney, Agent, or Firm—Mollie M. Yang; David L. Rose

[57] ABSTRACT

Compounds having the formula I:

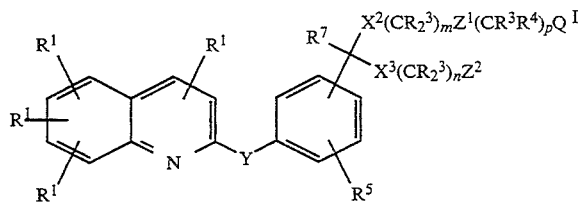

are antagonists of the actions of leukotrienes. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

11 Claims, No Drawings

HETEROARYL AND HALOARYL QUINOLINE

WO 87/05510 discloses compounds of the general formula:

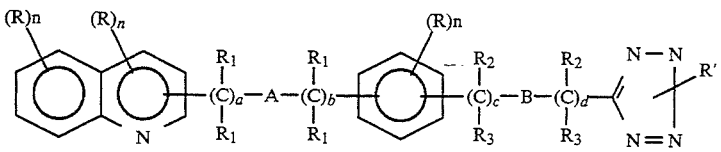

DERIVATIVES OF CYCLOPROPANEACETIC ACID AS LEUKOTRIENE ANTAGONISTS

BACKGROUND

The leukotrienes constitute a group of locally acting hormones, produced in living systems from arachidonic acid. The major leukotrienes are Leukotriene B4 (abbreviated at $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be is found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

Several classes of compounds exhibit the ability to inhibit the biosynthesis of leukotrienes in mammals, especially humans.

EP 181,568 describes a series of compounds of the general formula:

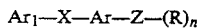

which differ from the present invention in not having a cycloalkyl or phenyl substituent (R) attached directly to the alkylene chain Z and in not having the Q substituent in the preferred embodiment of the present invention attached by a sulfur atom to the alkylene chain.

U.S. Pat. No. 4,631,287 contains compounds of the formula:

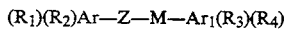

which differ from the present invention in that the $R_3$ and $R_4$ substituents which contain a carboxy group (corresponding to the Q substituent of the present invention) are attached directly to $Ar_1$ by an oxygen atom. Further, when they contain an aryl group, it is either attached directly to $Ar_1$ or is attached through an oxygen atom. Furthermore, $R_3$ or $R_4$ do not simultaneously include the Q substituent of the present invention and the cycloalkyl or phenyl substituent of the present invention.

EP 200,101 and Australian Patent application 56398/86 disclose compounds of the formula:

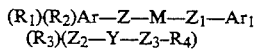

which differ from the compounds of the present invention in that the substituent unit ($Z_2$—Y—$Z_3$-$R_4$) does not simultaneously contain the cycloalkyl or phenyl and Q substituents of the present invention.

which differ from the compounds of the present invention in that they contain the heterocyclic tetrazole moiety which is absent from the present compounds, and in that the phenyl group present in the $R_2$ and $R_3$ substituents is unsubstituted.

Zamboni et al. in U.S. Pat. No. 5,102,881 describe the following compounds as inhibitors of leukotriene biosynthesis:

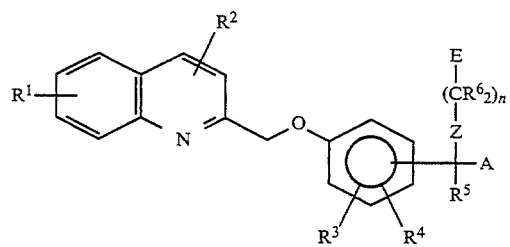

SUMMARY OF THE INVENTION

The present invention relates to haloaryl quinoline derivatives of cyclopropaneacetic acid having activity as leukotriene antagonists, to methods for their preparation, and to methods and pharmaceutical formulations for using these compounds in mammals (especially humans).

Because of their activity as leukotriene antagonists, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

DETAILED DESCRIPTION OF THE INVENTION

The compound of the invention are best realized by the Formula I:

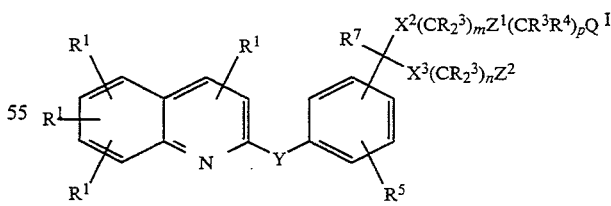

wherein:

$R^1$ is H, halogen, —$CF_3$, —CN, —$NO_2$, or —$N_3$;

$R^2$ is lower alkyl, lower alkenyl, lower alkynyl, —$CF_3$, —$CH_2F$, —$CHF_2$, Ph($R^{25}$)$_2$, $CH_2$Ph($R^{25}$)$_2$, or $CH_2CH_2$Ph($R^{25}$)$_2$, or two $R^2$ groups joined to the same atom may form a saturated ring of up to 8 members containing up to 2 heteroatoms chosen from O, S, and N;

$R^3$ is H or $R^2$;

$R^4$ is $R^3$, halogen, —$NO_2$, —CN, —$CF_3$, —$OR^3$, $N(R^3)_2$, $NR^3COR^7$, —$SR^2$, $S(O)R^2$, $S(O)_2R^2$, $CHR^7OR^3$, or $CHR^7SR^2$;

$CR^3R^4$ may be the radical of a standard amino acid;

$R^5$ is H, halogen, —$NO_2$, —$N_3$, —CN, —$SR^2$, —$S(O)R^2$, $S(O)_2R^2$, —$N(R^{12})_2$, —$OR^3$, —$COR^3$, or lower alkyl;

$R^6$ is —$(CH_2)_s$—$C(R^7)_2$—$(CH_2)_s$—$R^8$ or —$CH_2CON(R^{20})_2$;

$R^7$ is H or lower alkyl;

$R^8$ is A) a monocyclic or bicyclic heterocyclic radical containing from 3 to 12 nuclear carbon atoms and 1 or 2 nuclear heteroatoms selected from N, S, and O, with each ring in the heterocyclic radical being formed of 5 or 6 atoms, or B) the radical W—$R^9$;

$R^9$ contains up to 21 carbon atoms and is (1) a hydrocarbon radical or (2) an acyl radical of an organic acyclic or monocyclic carboxylic acid containing not more than 1 heteroatom in the ring;

$R^{10}$ is H, lower alkyl, or halogen;

$R^{11}$ is lower alkyl, —$COR^{14}$, $Ph(R^{25})_2$, $CH_2Ph(R^{25})_2$, or $CH_2CH_2Ph(R^{25})_2$;

$R^{12}$ is H or $R^{11}$, or two $R^{12}$ groups joined to the same N may form a saturated ring of 5 or 6 members comprising carbon atoms and up to two heteroatoms chosen from O, S, and N;

$R^{13}$ is lower alkyl, lower alkenyl, lower alkynyl, —$CF_3$, $Ph(R^{25})_2$, $CH_2Ph(R^{25})_2$, or $CH_2CH_2Ph(R^{25})_2$;

$R^{14}$ is H or $R^{13}$;

$R^{15}$ is H or $R^{11}$;

$R^{16}$ is H, lower alkyl, or OH;

$R^{17}$ is lower alkyl, lower alkenyl, lower alkynyl, $Ph(R^{25})_2$, $CH_2Ph(R^{25})_2$, or $CH_2CH_2Ph(R^{25})_2$;

$R^{18}$ is $R^{13}$;

$R^{19}$ is H, lower alkyl, lower alkenyl, lower alkynyl, —$CF_3$, Ph, $CH_2Ph$, or $CH_2CH_2Ph$;

$R^{20}$ is H, lower alkyl, $Ph(R^{25})_2$, $CH_2Ph(R^{25})_2$, or $CH_2CH_2Ph(R^{25})_2$, or two $R^{20}$ groups joined to the same N may form a saturated ring of 5 or 6 members comprising carbon atoms and up to two heteroatoms chosen from O, S, and N;

$R^{21}$ is H or $R^{17}$;

$R^{22}$, $R^{23}$, and $R^{24}$ is each independently H, lower alkyl, $CF_3$, $CF_2H$, $CH_2CF_3$, halogen, $OR^3$, $SR^2$, or an electron pair;

$R^{25}$ is H, —$CO_2R^7$, —$COR^7$, —CN, $CF_3$, $NO_2$, $SCF_3$, lower alkyl, —$SR^{26}$, —$OR^{27}$, $N(R^{27})_2$, $CON(R^{27})_2$, or halogen.

$R^{26}$ is lower alkyl, phenyl, or benzyl;

$R^{27}$ is $R^{26}$, H, or $COR^7$, or two $R^{27}$ groups joined to the same N may form a saturated ring of 5 or 6 members comprising carbon atoms and up to 2 heteroatoms chosen from O, S, and N;

m, n, and p is each independently 0–8;

m+p is 1–10 when $X^2$ is O, S, S(O), or $S(O)_2$ and $Z^1$ is a bond;

m+p is 0–10 when $Z^1$ is HET $(R^{22}R^{23}R^{24})$;

n+p is 0–10 when $X^2$ is $CR^3R^{16}$;

s is 0–3;

Q is tetrazol-5-yl, —$CO_2R^3$, —$CO_2R^6$, —CONH-$S(O)_2R^{13}$, —CN, —$CON(R^{20})_2$, —$NR^{21}S(O)_2R^{13}$, —$NR^{21}CON(R^{20})_2$, —$NR^{21}COR^{14}$, $OCON(R^{20})_2$, —$COR^{19}$, —$S(O)R^{18}$, —$S(O)_2R^{18}$, —$S(O)_2N(R^{20})_2$, —$\overline{NO}_2$, —$NR^{21}CO_2R^{17}$, —$C(N(R^{20})_2)$=$NR^{21}$, —$C(R^{19})$=NOH, or —$C(R^3)_2OH$; or if Q is $CO_2H$ and $R^4$ is —OH, —$CHR^7OH$, or —$NHR^3$, then Q and $R^4$ and the carbons through which they are attached may form a heterocyclic ring by loss of water;

W is S or $NR^3$;

$X^1$ is O, S, —S(O)—, —$S(O)_2$—, —$NR^3$, —$C(R^3)_2$—, or a bond;

$X^2$ and $X^3$ is each independently O, S, S(O), $S(O)_2$, $CR^3R^{16}$, or a bond;

Y is —$CR^3$=$CR^3$—, —$C(R^3)_2$—$X^1$, —$X^1$—$C(R^3)_2$—, —$C(R^3)_2$—$X^1$—$C(R^3)_2$—, —C≡C—, —CO—, —$NR^3CO$—, —$CONR^3$—, O, S, $NR^3$, or

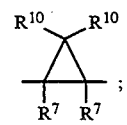

$Z^1$ is HET $(R^{22}R^{23})$ or a bond;

$Z_2$ is HET $(R^{22}R^{23}R^{24})$;

HET is benzene, pyridine, furan, thiophene, thiazole, pyrazine, benzimidazole, quinoline, benzothiazole, 5,6,7,8-tetrahydroquinoline, or 1,2,5-thiadiazole;

or a pharmaceutically acceptable salt thereof.

Preferred compounds of Formula I are those of Formula Ia:

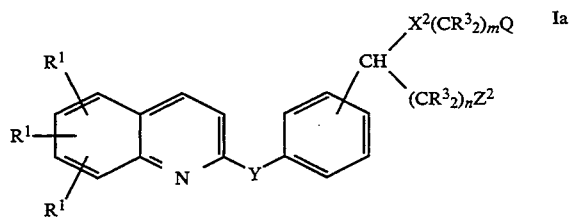

wherein:

$R^1$ is H, halogen, —$CF_3$;

m and n is each independently 1–6;

Q is $CO_2R^3$, $CO_2R^6$, —$CONHS(O)_2R^{13}$, tetrazol-5-yl, or $C(R^3)_2OH$;

$X^2$ is S or O;

Y is —CH=CH—, —$CH_2$—$CH_2$, —C≡C—, or —$CH(CH_2)CH$—;

$Z_2$ is HET $(R^{22}R^{23})$;

HET is benzene, thiophene, or pyridine;

and the remaining substituents are as defined for Formula I.

A group of most preferred compounds of Formula I is described by Formula Ib:

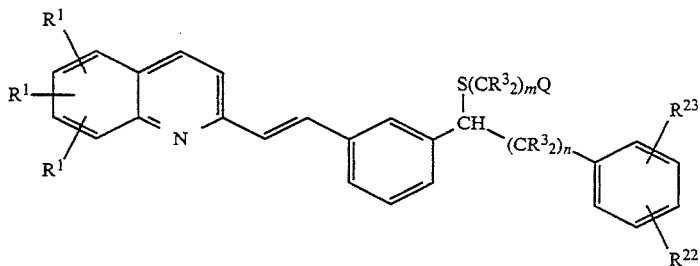

wherein:
R¹ is H, halogen or CF₃;
R³ is H or lower alkyl, or two R³ joined to the same carbon may form a ring from 3 to 6 members, optionally containing one oxygen or sulfur;
R²² and R²³ is each independently H, halogen, or lower alkyl;
m and n is each independently 1-5;
Q is —CO₂R³, tetrazol-5-yl, or —CONHS(O)₂R¹³;
and the remaining substituents are as defined for Formula I.

Definitions

The following abbreviations have the indicated meanings:
Ac=acetyl
AIBN=2.2-azobisisobutyronitrile
Bmz=benzimidazolyl
Bn=benzyl
Btz=benzothiazolyl
DHP=2.3-dihydro-4H-pyran
DIAD=diisopropyl azodicarboxylate
DIBAL=diisobutyl aluminum hydride
DIPHOS=1,2-bis(diphenylphosphino)ethane
DMAP=4-(dimethylamino)pyridine
DMF=N,N-dimethylformamide
DMSO=dimethyl sulfoxide
Et₃N=triethylamine
Fl=2- or 3-furyl
Fur=furandiyl
KHMDS=potassium hexamethyldisilazane
LDA=lithium diisopropylamide
MS=methanesulfonyl=mesyl
MsO=methanesulfonate=mesylate
NBS=N-bromosuccinimide
NCS=N-chlorosuccinimide
NMO=N-methylmorpholine N-oxide
NSAID=non-steroidal anti-inflammatory drag
PCC=pyridinium chlorochromate
PDC=pyridinium dichromate
Ph=phenyl
Phe=benzenediyl
PPTS=pyridinium p-toluene sulfonate
pTSA=p-toluene sulfonic acid
Py=pyridyl
Pye=pyridinediyl
Pz=pyrazinyl
Qn=quinolinyl
r.t.=room temperature
rac.=racemic
Tdz=1,2,5-thiadiazol-3,4-diyl
Tf=trifluoromethanesulfonyl=triflyl
TfO=trifluoromethanesulfonate=triflate
Th=2- or 3-thienyl
THF=tetrahydrofuran
Thi=thiophenediyl
THP=tetrahydropyran-2-yl
THQ=5,6,7,8-tetrahydroquinolinyl
Thz=thiazolyl
Tl=1,2,5-thiadiazolyl
TLC=thin layer chromatography
TPAP=tetrapropylammonium perruthenate
Ts=p-toluenesulfonyl=tosyl
TsO=p-toluenesulfonate=tosylate
Tz=1H (or 2H)-tetrazol-5-yl
C₃H₅=allyl Alkyl group abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl The terms alkyl, alkenyl, and alkynyl mean linear, branched, and cyclic structures and combinations thereof.

The term "alkyl" includes "cycloalkyl" and "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propyl-nonyl, and the like.

"Lower alkyl" includes "lower cycloalkyl" and means alkyl groups of from 1 to 7 carbon atoms. Examples of lower alkyl groups include methyl, ethyl, propyl, isopropyl, butyl, s- and t-butyl, pentyl, hexyl, heptyl, and the like.

"Cycloalkyl" includes "lower cycloalkyl" and means a hydrocarbon containing one or more rings of from 3 to 12 carbon atoms, with the hydrocarbon having up to a total of 20 carbon atoms. Examples of cycloalkyl groups are cyclopropyl, cyclopentyl, cycloheptyl, aldamantyl, cyclododecylmethyl, 2-ethyl-1-bicyclo[4.4.0]decyl and the like.

"Lower cycloalkyl" means a hydrocarbon containing one or more rings of from 3 to 7 carbon atoms, with the hydrocarbon having up to a total of 7 carbon atoms. Examples of lower cycloalkyl groups are cyclopropyl, cyclopropylmethyl, cyclobutyl, 2-cyclopentylethyl, cycloheptyl, bicyclo[2.2.1]hept-2-yl and the like.

The term "alkenyl" includes "cycloalkenyl" and "lower alkenyl" and means alkenyl groups of 2 to 20 carbon atoms. Examples of alkenyl groups include allyl, 5-decen-1-yl, 2-dodecen-1-yl, and the like.

"Lower alkenyl" includes "lower cycloalkenyl" and means alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl and the like.

"Cycloalkenyl" includes "lower cycloalkenyl" and means alkenyl groups of 3 to 20 carbon atoms, which include a ring of 3 to 12 carbon atoms, and in which the alkenyl double bond may be located anywhere in the structure. Examples of cycloalkenyl groups are cyclopropen-1-yl, cyclohexen-3-yl, 2-vinyladamant-1-yl, 5-methylenedodec-1-yl, and the like.

"Lower cycloalkenyl" means alkenyl groups of 3 to 7 carbon atoms which include a ring of 3 to 7 carbon atoms and in which the double bond may be located anywhere in the structure. Examples of lower cycloalkenyl groups are cyclopropen-1-yl, cyclohexen-3-yl, 2-cyclopentylethen-1-yl, and the like.

The term "alkynyl" includes "cycloalkynyl" and "lower alkynyl" and means alkynyl groups of 2 to 20 carbon atoms. Examples of alkynyl groups are ethynyl, 2-pentadecyn-1-yl, 1-eicosyn-1-yl, and the like.

"Lower alkynyl" includes "lower cycloalkynyl" and means alkynyl groups of 2 to 7 carbon atoms. Examples of lower alkynyl groups include ethynyl, propargyl, 3-methyl-1-pentynyl, 2-heptynyl, and the like.

"Cycloalkynyl" includes "lower cycloalkynyl" and means alkynyl groups of 5 to 20 carbon atoms, which include a ring of 3 to 20 carbon atoms. The alkynyl triple bond may be located anywhere in the group, with the proviso that if it is within a ring, such a ring must be 10 members or greater. Examples of cycloalkynyl are cyclododecyn-3-yl, 3-cyclohexyl-1-propyn-1-yl, and the like.

"Lower cycloalkynyl" means alkynyl groups of 5 to 7 carbon atoms which include a ring of 3 to 5 carbon atoms. Examples of lower cycloalkynyl are cyclopropylethynyl, 3-(cyclobutyl)-1-propynyl, and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylthio" means alkylthio groups of from 1 to 7 carbon atoms of a straight, branched, or cyclic configuration. Examples of lower alkylthio groups include methylthio, propylthio, isopropylthio, cycloheptylthio, etc. By way of illustration, the propylthio group signifies —$SCH_2CH_2CH_3$.

"Lower alkylsulfonyl" means alkylsulfonyl groups of from 1 to 7 carbon atoms of a straight, branched, or cyclic configuration. Examples of lower alkylsulfonyl groups are methylsulfonyl, 2-butylsulfonyl, cyclohexylmethylsulfonyl, etc. By way of illustration the 2-butylsulfonyl group signifies —$S(O)_2CH(CH_3)CH_2CH_3$.

The term "alkylcarbonyl" includes "lower alkylcarbonyl" and means alkylcarbonyl groups of 1 to 20 carbon atoms of a straight, branched, or cyclic configuration. Examples of alkylcarbonyl groups are formyl, 2-methylbutanoyl, octadecanoyl, 11-cyclohexylundecanoyl and the like. Thins, the 11-cyclohexylundecanoyl group is c—Hex—$(CH_2)_{10}$—CO—.

"Lower alkylcarbonyl" means alkylcarbonyl groups of from 1 to 8 carbon atoms of a straight, branched, or cyclic configuration. Examples of lower alkylcarbonyl groups are formyl, 2-methylbutanoyl, cyclohexylacetyl, etc. By way of illustration, the 2-methylbutanoyl groups signifies —$COCH(CH_3)CH_2CH_3$.

The term $Ph(R^{25})_2$ indicates a phenyl group substituted with two $R^{25}$ substituents.

Halogen includes F, Cl, Br, and I.

It is intended that the definitions of any substituent (e.g., $R^3$, $R^{25}$, etc.) in a particular molecule be independent of its definitions elsewhere in the molecule. Thus, —$N(R^3)_2$ represents —$NHH$, —$NHCH_3$, —$NHC_6H_5$, etc.

The rings formed when two $R^2$ groups join through the same atom include cyclopropane, cyclobutane, cyclopentane, cyclohexane, cycloheptane, cyclooctane, oxetane, tetrahydrofuran, tetrahydropyran, tetrahydrothiophene, tetrahydrothiopyran, pyrrolidine, piperidine, morpholine, thiamorpholine, piperazine, and the like.

The heterocycles formed when two $R^{12}$, $R^{20}$, or $R^{27}$ groups join through N include pyrrolidine, pipeddine, morpholine, thiamorpholine, piperazine, and N-methylpiperazine.

When $Q^1$ and $R^4$ and the carbons through which they are attached form a ring, the rings thus formed include lactones, lactams, and thiolactones.

The prodrug esters of Q (i.e., when $Q=CO_2R^6$) are intended to include the esters such as are described by Saari et al., J. Med. Chem., 21, No. 8, 746–753 (1978), Sakamoto et al., Chem. Pharm. Bull., 32, No. 6, 224 1–2248 (1984) and Bundgaard et al., J. Med. Chem., 30, No. 3, 451–454 (1987).

Within the definition of RS, some representative monocyclic or bicyclic heterocyclic radicals are:
2,5-dioxo-1-pyrrolidinyl,
(3-Pyridinylcarbonyl)amino,
1,3-dihydro-1,3-dioxo-2H-isoindol-2-yl,
1,3-dihydro-2H-isoindol-2-yl,
2,4-imidazolinedion-1-yl,
2,6-piperidinedion-1-yl,
2-imidazolyl,
2-oxo-1,3-dioxolen-4-yl,
piperidin-1-yl,
morpholin-1-yl, and
piperazin-1-yl.

The term "standard amino acid" means the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine, and valine. (See F. H. C. Crick, Symposium of the Society of Experimental Biology, 1958 (12), p. 140).

Optical Isomers—Diastcreomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, myocardial ischemia, hypertension, platelet aggregation and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological or infectious stimuli, 1 1) trauma or shock states such as bum injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are: (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, or anti-allergic use is from about 0.00 1 mg to about 25 mg (preferably from 0.01 mg to about 1 mg) of a compound of Formula I per kg of body weight per day and for cytoprotective use is from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g., from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 1 00 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Phamaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the an of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carders are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |

| Capsule | mg/capsule |
|---|---|
| | 500 |
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combinations with Other Drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) propionic acid derivatives;
(2) acetic acid derivatives;
(3) fenamic acid derivatives;
(4) oxicams; and
(5) biphenylcarboxylic acid derivatives,
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO—Na$^+$ or —CH$_2$CH$_2$COO—Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structurally related acetic acid derivatives having similar analgesic and anti-inflammatory properties are also intended to be encompassed by this group.

Thus, "acetic acid derivatives" as defined herein are nonnarcotic analgesics/non-steroidal anti-inflammatory drugs having a free —CH$_2$COOH group (which optionally can be in the form of a pharmaceutically acceptable salt group, e.g. —CH$_2$COO—Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

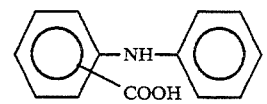

which can bear a variety of substituents and in which the free —COOH group can be in the form of a pharmaceutically acceptable salt group, e.g., —COO—Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

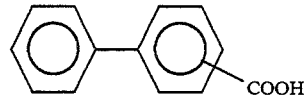

which can bear a variety of substituents and in which the free —COOH group can be in the form of a pharmaceutically acceptable salt group, e.g., —COO—Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

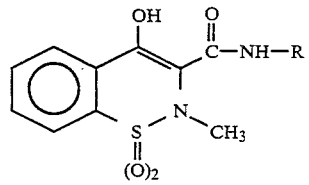

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., *Pharmaprojects*), may also be used: 480156S, AA861, AD1590, AFP802, AFP860, AI77B, AP504, AU8001, BPPC, BW540C, CHINOIN 127, CNI00, EB382, EL508, F1044, GV3658, ITF182, KCNTEI6090, KME4, LA2851, MR714, MR897, MY309, ONO3144, PR823, PVI02, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin.

Pharmaceutical compositions comprising the Formula I compounds may also contain inhibitors of the biosynthesis of the leukotrienes such as are disclosed in EP 138,481 (Apr. 24,1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the an such as those disclosed in EP Application Nos. 56,172 (July 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,96 1. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, 316, 126–131 (1985), and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of the present invention can be prepared according to the following methods. In these schemes:

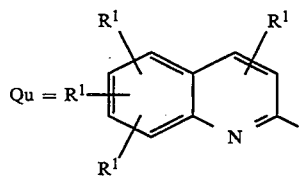

METHOD A

Allyl or vinylmagnesium bromide is added to the aldehyde III to yield IV. (A description of the formation of III where Y is CH=CH is given in the Examples. For Y=CH$_2$CH$_2$ and 1,2-cyclopropyl, see U.S. Pat. No. 5,104,882, Example 3, Step 2 and Styrene 4 respectively.) The homoallylic or allylic alcohol IV is then treated with the suitable bromide or iodide V in the presence of Pd at 100° C. to give VI. Chiral reduction of the ketone is done using a reagent such as (−)-B-chlorodiisopinocampheylborane. Formation of the mesylate and substitution by the thiol VIII in the presence of a base such as NaH or Cs$_2$CO$_3$ affords IX. When Q is an ester, hydrolysis yields the acid X. The epimer of IX can be obtained by using the (+) enantiomer of the chiral reagent for the reduction of VI.

METHOD B

Starting from XI, the synthesis is like Method A, except that the chiral reducing agent is the oxazaborolidine XIV. Deprotection of the tetrahydropyranyl protecting group is performed with pyridinium p-toluenesulfonate in methanol and the primary alcohol is oxidized to the aldehyde XVII with MnO$_2$. The quinoline moiety is added at the end of the synthesis by a Wittig coupling reaction between XVII and the phosphonium XVIIa in the presence of a base such as potassium t-butoxide.

METHOD C

Vinylmagnesium bromide is added to the aldehyde III followed by oxidation to give enone XIX. Then, an appropriate copperzincate reagent XX (prepared from the corresponding iodide, zinc powder and copper cyanide) is added to the enone XIX in the presence of chlorotrimethylsilane to yield, after hydrolysis of the enol ether, the ketone XXI. Chiral reduction gives the alcohol XXII. Alternatively, this alcohol can be obtained by addition of the appropriate copper-zincate reagent XXIII onto the aldehyde III in the presence of boron trifluoride etherate followed by oxidation and chiral reduction. Mesylate formation followed by displacement by the thiol VIII affords XXIV. When Q is an ester, hydrolysis yields the carboxylate XXV.

METHOD D

The β-keto ester XXVI (see U.S. Pat. No. 5,104,882) is alkylated with the appropriate reagent XXVII (such as 2-chloromethylpyridine) in the presence of a base such as NaH or t-BuOK to yield XXVIII. Decarbomethoxylation is accomplished by heating under acid or neutral conditions and the resulting ketone XXIX is reduced enantioselectively to the alcohol XXX. Mitsunobu inversion (Synthesis, pp 1–28, 1981) using thiolacetic acid as the nucleophile gives the thioacetate XXXI. Treatment with hydrazine generates the corresponding thiol which, upon reaction with a suitable mesylate XXXII followed by hydrolysis, yields the carboxylate XXXIII. Alternatively, the thiol can be treated with a substituted acrylic acid XXXIV to yield carboxylate XXXV.

METHOD E

Aldehyde III is converted into epoxide XXXVI using trimethylsulfoxonium ylid. Addition of a suitable organolithium reagent XXXVII gives the racemic alcohol XXXVIII.

Oxidation using tetrapropylammonium perruthenate and N-methylmorpholine N-oxide followed by chiral reduction gives alcohol XXX. Transformation of the latter into carboxylate XXXIII is accomplished as in Method C or D.

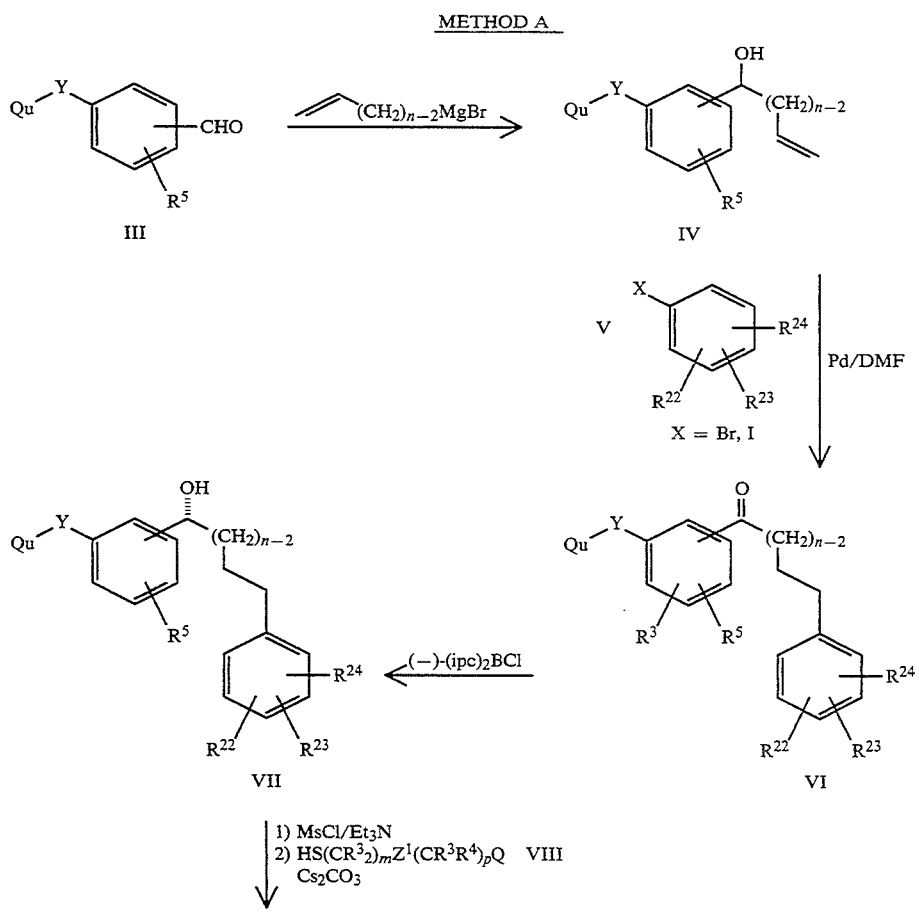

METHOD A

-continued
METHOD A
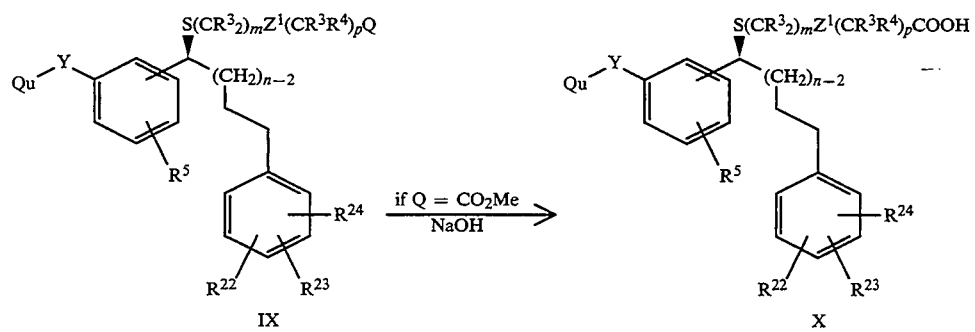
METHOD B
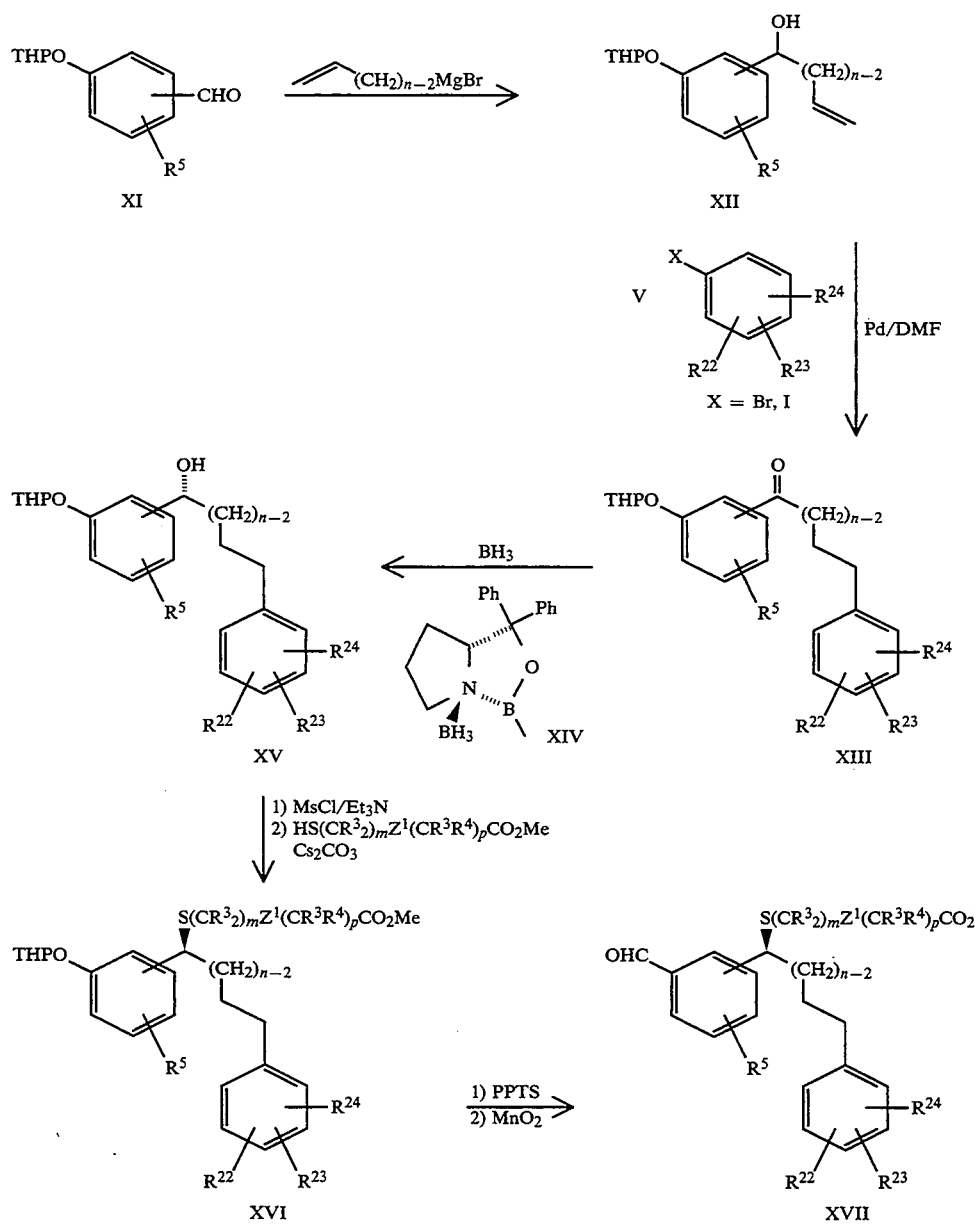

-continued
METHOD B
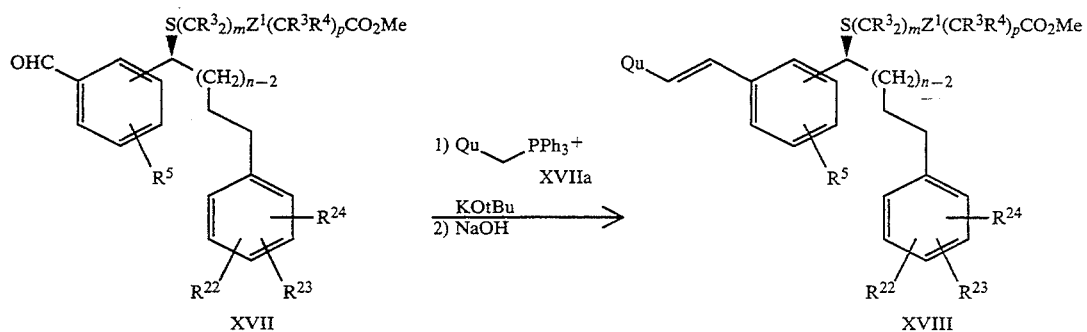
METHOD C
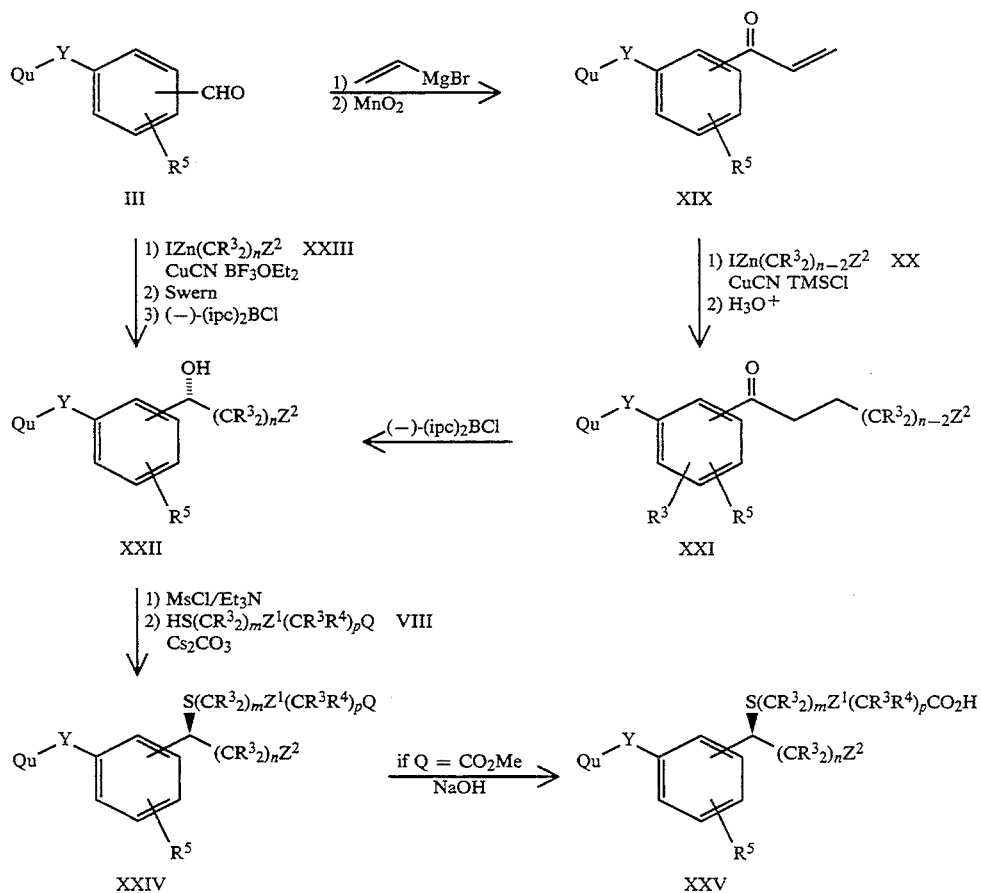
METHOD D
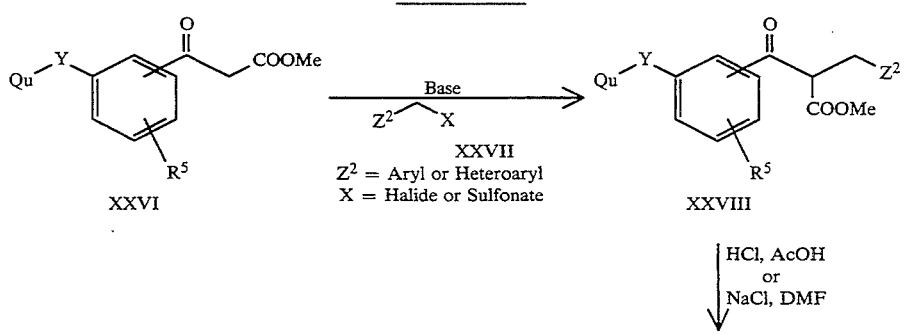

METHOD D
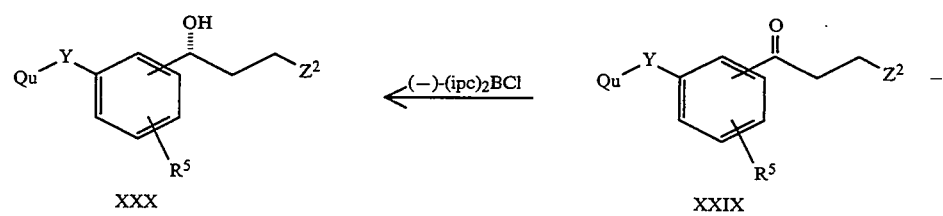
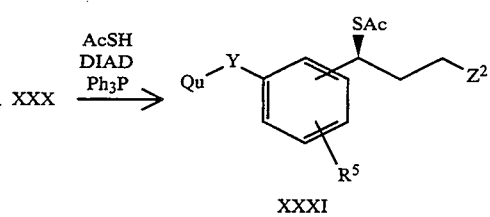
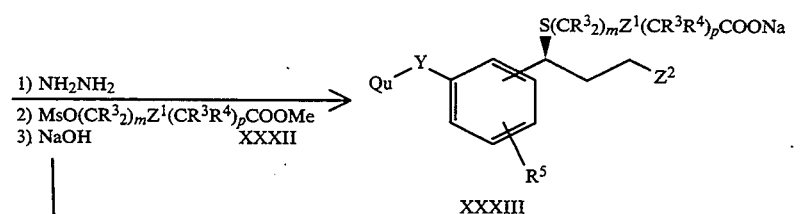
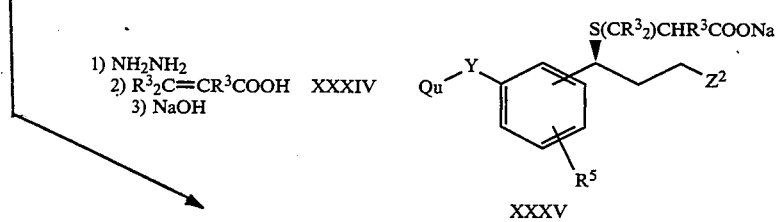
METHOD E
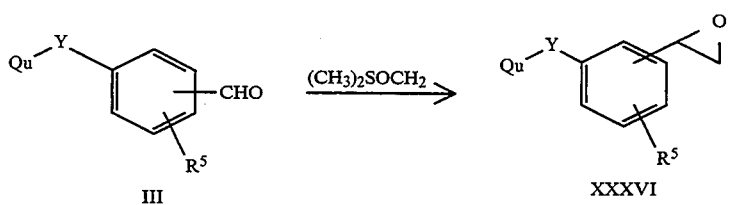
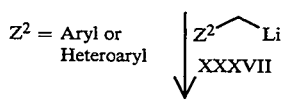
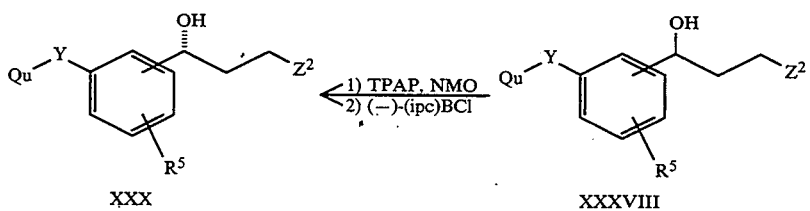
as in
Method C or D

METHOD E

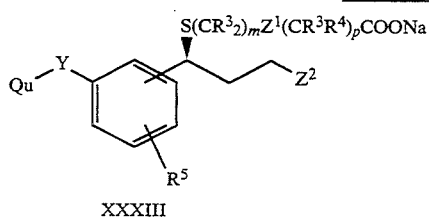

XXXIII

-continued

REPRESENTATIVE COMPOUNDS

Tables 1 and 2 illustrate compounds of formulae Ic and Id, which are representative of the present invention. Elemental analysis data are presented in Table 3.

TABLE 1

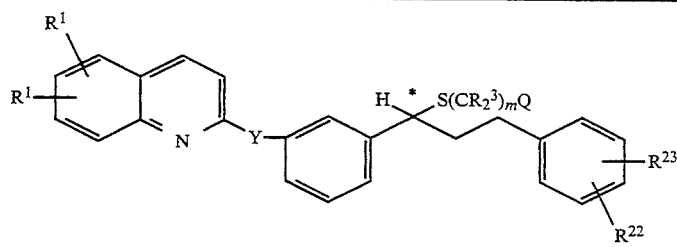

Ic

| Ex. | $R^1, R^1$ | Y | $(CR_2{}^3)_mQ$ | $R^{22}, R^{23}$ | * |
|---|---|---|---|---|---|
| 1 | 6,7-$F_2$ | —CH=CH— | $CH_2(1,1$-c-Pr$)CH_2CO_2H$ | 2-F, H | (R) |
| 2 | 6,7-$F_2$ | —CH=CH— | $CH_2(1,1$-c-Pr$)CH_2CO_2H$ | 2-Cl, H | (R) |
| 3 | 6,7-$F_2$ | —CH=CH— | $CH_2(1,1$-c-Pr$)(CH_2CO_2H$ | 2-Br, H | (R) |
| 4 | 6,7-$F_2$ | —CH=CH— | $CH_2(1,1$-c-Pr$)CH_2CO_2H$ | 3-F, H | rac |
| 5 | 6,7-$F_2$ | —CH=CH— | $CH_2(1,1$-c-Pr$)CH_2CO_2H$ | 3-Cl, H | rac |
| 6 | 6,7-$F_2$ | —CH=CH— | $CH_2(1,1$-c-Pr$)CH_2CO_2H$ | 3-Br, H | (R) |
| 7 | 6,7-$F_2$ | —CH=CH— | $CH_2(1,1$-c-Pr$)CH_2CO_2H$ | 4-F, H | (R) |
| 8 | 6,7-$F_2$ | —CH=CH— | $CH_2(1,1$-c-Pr$)CH_2CO_2H$ | 4-Cl, H | (R) |
| 9 | 6,7-$F_2$ | —CH=CH— | $CH_2(1,1$-c-Pr$)CH_2CO_2H$ | 4-Br, H | (R) |
| 10 | 6,8-$F_2$ | —$CH_2$—$CH_2$— | $CH_2C(CH_3)_2CH_2CO_2H$ | 4-Br, H | rac |
| 11 | 6,8-$F_2$ | —$CH_2$—$CH_2$— | $CH_2C(CH_3)_2CH_2CO_2H$ | 4-Br, H | rac |
| 12 | 6,8-$F_2$ | —$CH_2$—$CH_2$— | $CH_2C(CH_3)_2CH_2CO_2H$ | 4-Br, H | rac |
| 13 | 6,8-$F_2$ | —$CH_2$—$CH_2$— | $CH_2C(CH_3)_2CH_2CO_2H$ | 4-Br, H | rac |
| 14 | 6,8-$F_2$ | —$CH_2$—$CH_2$— | $CH_2C(CH_3)_2CH_2CO_2H$ | 4-Br, H | rac |
| 15 | 6,8-$F_2$ | —$CH_2$—$CH_2$— | $CH_2C(CH_3)_2CH_2CO_2H$ | 4-Br, H | rac |
| 16 | 6,8-$F_2$ | —$CH_2$—$CH_2$— | $CH_2C(CH_3)_2CH_2CO_2H$ | 4-Br, H | rac |
| 17 | 6,8-$F_2$ | —$CH_2$—$CH_2$— | $CH_2C(CH_3)_2CH_2CO_2H$ | 4-Br, H | rac |
| 18 | 6,8-$F_2$ | —$CH_2$—$CH_2$— | $CH_2C(CH_3)_2CH_2CO_2H$ | 4-Br, H | rac |
| 19 | 6,7-$F_2$ | —C≡C— | $(1,1$-c-Pr$)CH_2CO_2H$ | 4-Br, H | rac |
| 20 | 6,7-$F_2$ | —C≡C— | $(1,1$-c-Pr$)CH_2CO_2H$ | 4-Br, H | rac |
| 21 | 6,7-$F_2$ | —C≡C— | $(1,1$-c-Pr$)CH_2CO_2H$ | 4-Br, H | rac |
| 22 | 6,7-$F_2$ | —C≡C— | $(1,1$-c-Pr$)CH_2CO_2H$ | 4-Br, H | rac |
| 23 | 6,7-$F_2$ | —C≡C— | $(1,1$-c-Pr$)CH_2CO_2H$ | 4-Br, H | rac |
| 24 | 6,7-$F_2$ | —C≡C— | $(1,1$-c-Pr$)CH_2CO_2H$ | 4-Br, H | rac |
| 25 | 6,7-$F_2$ | —C≡C— | $(1,1$-c-Pr$)CH_2CO_2H$ | 4-Br, H | rac |
| 26 | 6,7-$F_2$ | —C≡C— | $(1,1$-c-Pr$)CH_2CO_2H$ | 4-Br, H | rac |
| 27 | 6,7-$F_2$ | —C≡C— | )$1,1$-c-Pr$)CH_2CO_2H$ | 4-Br, H | rac |
| 28 | 6,7-$F_2$ | —CH=CH— | $CH_2(1,1$-c-Pr$)CH_2CO_2H$ | H, H | (R) |
| 29 | 7-Cl, H | —CH=CH— | $CH_2(1,1$-c-Pr$)CH_2CO_2H$ | H, H | rac |
| 30 | 6,7-$Cl_2$ | —CH=CH— | $CH_2(1,1$-c-Pr$)CH_2CO_2H$ | 2-F, 4-$CH_3$ | rac |
| 31 | 6-F, H | —CH=CH— | $CH_2(1,1$-c-Pr$)CH_2CO_2H$ | 2-c-Pr, 4-F | rac |
| 32 | 6-Cl, H | —CH=CH— | $CH_2(1,1$-c-Pr$)CH_2CO_2H$ | 4-O-c-Pr, H | rac |
| 33 | 7-F, H | —CH=CH— | $CH_2(1,1$-c-Pr$)CH_2CO_2H$ | 2-O-c-Pr, 4-F | rac |
| 34 | 7-F, H | —CH=CH— | $CH_2(1,1$-c-Pr$)CH_2CO_2H$ | 2-F, 4-O-c-Pr | rac |
| 35 | 7-F, H | —CH=CH— | $CH_2(1,1$-c-Pr$)CH_2CO_2H$ | 2-F, 4-c-Pr | rac |
| 36 | 6-$CF_3$, H | —CH=CH— | $CH_2(1,1$-c-Pr$)CH_2CO_2h$ | 2-c-Pr, 4-Cl | rac |
| 37 | 6,7-$Cl_2$ | —CH=CH— | $CH_2(1,1$-c-Pr$)CH_2CO_2H$ | 2-$CF_3$, H | rac |
| 38 | 7-$CF_3$, H | —CH=CH— | $CH_2(1,1$-c-Pr$)CH_2CO_2H$ | 2-$CF_2H$, 4-O-c-Pr | rac |

TABLE 2

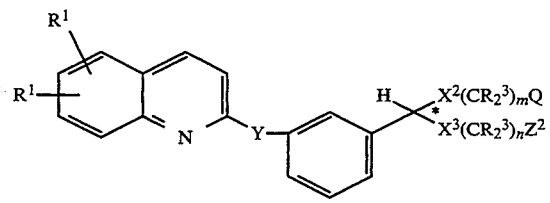

Id

| EX. | $R^1, R^1$ | Y | $X^2(CR_2^3)_mQ$ | $X^3(CR_2^3)_nZ^2$ | * |
|---|---|---|---|---|---|
| 39 | 7-Cl, H | —CH=CH— | SCH$_2$C(S)H(Me)CO$_2$H | CH$_2$CH$_2$-3-Py | (S) |
| 40 | 7-Cl, H | —CH=CH— | SCH$_2$C(Me)$_2$CH$_2$CO$_2$H | CH$_2$CH$_2$-3-Py | (R) |
| 41 | 7-Cl, H | —CH$_2$CH$_2$— | SC(S)H(Me)CH$_2$CO$_2$H | CH$_2$CH$_2$-3-Py | (R) |
| 42 | 7-Cl, H | —CH$_2$CH$_2$— | CH$_2$CH$_2$C(Me)$_2$CH$_2$CO$_2$H | SCH$_2$-2-Py | (S) |
| 43 | 7-Cl, H | —CH$_2$CH$_2$— | CH$_2$CH$_2$C(Me)$_2$CH$_2$CO$_2$H | S—CH$_2$CH$_2$-2-Py | (S) |
| 44 | 7-Cl, H | —CH$_2$CH$_2$— | SC(Me)$_2$CH$_2$CO$_2$H | CH$_2$CH$_2$-2-Py | (R) |
| 45 | 7-Cl, H | —CH$_2$CH$_2$— | SCH$_2$(1,1-c-Pr)CH$_2$CO$_2$H | CH$_2$CH$_2$-2-Py | (R) |
| 46 | 7-Cl, H | —CH$_2$CH$_2$— | SCH$_2$(1,1-c-Pr)CH$_2$CO$_2$H | CH$_2$CH$_2$-3-Py | (R) |
| 47 | 7-Cl, H | —CH$_2$CH$_2$— | SCH$_2$(1,1-c-Pr)CH$_2$CO$_2$H | CH$_2$CH$_2$CH$_2$-3-Py | (R) |
| 48 | 7-Cl, H | —CH$_2$CH$_2$— | CH$_2$CH$_2$(1,2-(4-Cl—Phe))CH$_2$CO$_2$H | SCH$_2$CH$_2$-2-Py | (R) |
| 49 | 7-Cl, H | —CH$_2$CH$_2$— | SCH$_2$(1,1-c-Pr)CH$_2$CO$_2$H | CH$_2$CH$_2$-2-(5-Br—Py) | (R) |
| 50 | 7-Cl, H | —CH$_2$CH$_2$— | SCH$_2$(1,1-c-Pr)CH$_2$CO$_2$H | CH$_2$CH$_2$-2-Pz | rac |
| 51 | 7-Cl, H | —CH$_2$CH$_2$— | SCH$_2$(1,1-c-Pr)CH$_2$CO$_2$H | CH$_2$CH$_2$-2-(4-Me—Thz) | (R) |
| 52 | 7-Cl, H | —CH$_2$CH$_2$— | SCH$_2$(1,1-c-Pr)CH$_2$CO$_2$H | CH$_2$CH$_2$-2-Qn | (R) |
| 53 | 7-Cl, H | —CH$_2$CH$_2$— | SCH$_2$(1,1-c-Pr)CH$_2$CO$_2$H | CH$_2$CH$_2$-2-(7-Cl—Qn) | (R) |
| 54 | 7-Cl, H | —CH$_2$CH$_2$— | CH$_2$CH$_2$(1-2-Phe)CH$_2$CO$_2$H | S-2-Bmz | (S) |
| 55 | 7-Cl, H | —CH$_2$CH$_2$— | SCH$_2$(1,1-c-Pr)CH$_2$CO$_2$H | CH$_2$CH$_2$-2-Btz | rac |
| 56 | 7-Cl, H | -1,2-c-Pr— | SCH$_2$(1,1-c-Pr)CH$_2$CO$_2$H | CH$_2$CH$_2$-2-Py | (R) |
| 57 | 6,7-F$_2$ | —CH=CH— | SCH$_2$(1,1-c-Pr)CH$_2$CO$_2$H | CH$_2$CH$_2$-2-Py | (R) |
| 58 | 6,7-F$_2$ | —CH=CH— | SCH$_2$(1,1-c-Pr)CH$_2$CO$_2$H | CH$_2$CH$_2$-2-THQ | (R) |
| 59 | 6,7-F$_2$ | —CH=CH— | SCH$_2$(1,1-c-Pr)CH$_2$CO$_2$H | CH$_2$CH$_2$-2-Fl | (R) |
| 60 | 6,7-F$_2$ | —CH=CH— | SCH$_2$(1,1-c-Pr)CH$_2$CO$_2$H | CH$_2$CH$_2$-2-(4-i-Pr—Thz) | (R) |
| 61 | 6,7-F$_2$ | —CH=CH— | SCH$_2$(1,1-c-Pr)CH$_2$CO$_2$H | CH$_2$CH$_2$-3-Tl | rac |
| 62 | 7-Cl, H | —CH=CH— | SCH$_2$(1,1-c-Pr)CH$_2$CO$_2$H | CH$_2$CH$_2$-3-(4-Cl—Tl) | rac |
| 63 | 6,7-F$_2$ | —CH$_2$CH$_2$— | SCH$_2$(1,1-c-Pr)CH$_2$CO$_2$H | CH$_2$CH$_2$-3-Th | rac |
| 64 | 6,7-F$_2$ | —CH=CH— | SCH$_2$(1,1-c-Pr)CH$_2$Tz | CH$_2$CH$_2$(2-Br—Ph) | rac |
| 65 | 6,7-F$_2$ | —CH=CH— | SCH$_2$(1,1-c-Pr)CH$_2$CONHS(O)$_2$Me | CH$_2$CH$_2$(2-Cl—Ph) | rac |
| 66 | 6,7-F$_2$ | —CH=CH— | SCH$_2$(1,1-c-Pr)CH$_2$CONH-t-Bu | CH$_2$CH$_2$(2-F—Ph) | rac |
| 67 | 6,7-F$_2$ | —CH=CH— | SCH$_2$(1,1-c-Pr)CH$_2$C(Me)$_2$OH | CH$_2$CH$_2$(4-SMe—Ph) | rac |
| 68 | 6,7-F$_2$ | —CH=CH— | SCH$_2$(1,1-c-Pr)CH$_2$S(O)$_2$NH$_2$ | CH$_2$CH$_2$(4-SCF$_3$—Ph) | rac |

TABLE 3

| Ex. | | Calc. | | | Found | | |
|---|---|---|---|---|---|---|---|
| | | C | H | N | C | H | N |
| 1 | C$_{32}$H$_{27}$F$_3$NO$_2$SNa · 2.5H$_2$O | 62.71 | 5.23 | 2.29 | 62.76 | 5.16 | 2.22 |
| 6 | C$_{32}$H$_{27}$BrF$_2$NO$_2$SNa · 1H$_2$O | 58.94 | 4.54 | 2.15 | 58.87 | 4.26 | 2.17 |
| 7 | C$_{32}$H$_{27}$F$_3$NO$_2$SNa · 3H$_2$O | 61.63 | 5.33 | 2.25 | 61.56 | 5.18 | 2.20 |
| 8 | C$_{32}$H$_{27}$ClF$_2$NO$_2$SNa · 1.5H$_2$O | 62.69 | 4.93 | 2.28 | 62.33 | 5.00 | 2.27 |
| 9 | C$_{32}$H$_{27}$BrF$_2$NO$_2$SNa · 2.5H$_2$O | 56.97 | 4.74 | 2.08 | 56.92 | 4.60 | 1.88 |
| 39 | C$_{29}$H$_{26}$ClN$_2$O$_2$SNa · 2H$_2$O | 62.08 | 5.39 | 4.99 | 61.90 | 5.41 | 4.96 |
| 40 | C$_{31}$H$_{30}$ClN$_2$O$_2$SNa · 1.8H$_2$O | 63.59 | 5.78 | 4.78 | 63.52 | 5.93 | 4.65 |
| 41 | C$_{29}$H$_{28}$ClN$_2$O$_2$SNa · 1.1H$_2$O | 63.69 | 5.57 | 5.12 | 63.75 | 5.59 | 5.19 |
| 42 | C$_{31}$H$_{32}$ClN$_2$O$_2$SNa · 1H$_2$O | 64.97 | 5.98 | 4.89 | 65.09 | 5.95 | 4.88 |
| 43 | C$_{32}$H$_{34}$ClN$_2$O$_2$SNa · 2H$_2$O | 63.51 | 6.33 | 4.63 | 63.77 | 6.44 | 4.56 |
| 44 | C$_{30}$H$_{30}$ClN$_2$O$_2$SNa · 1H$_2$O | 64.45 | 5.77 | 5.01 | 64.28 | 5.94 | 5.07 |
| 45 | C$_{31}$H$_{30}$ClN$_2$O$_2$SNa · 0.4H$_2$O | 66.45 | 5.54 | 5.00 | 66.41 | 5.44 | 5.00 |
| 46 | C$_{31}$H$_{30}$ClN$_2$O$_2$SNa · 1.3H$_2$O | 64.58 | 5.70 | 4.86 | 64.62 | 5.63 | 4.71 |
| 52 | C$_{35}$H$_{32}$ClN$_2$O$_2$SNa · 1.8H$_2$O | 66.14 | 5.65 | 4.41 | 66.10 | 5.70 | 4.34 |
| 53 | C$_{35}$H$_{31}$Cl$_2$N$_2$O$_2$SNa · 1.1H$_2$O | 63.94 | 5.09 | 4.26 | 63.86 | 5.04 | 4.33 |
| 55 | C$_{33}$H$_{30}$ClN$_2$O$_2$Na · 2.5H$_2$O | 60.64 | 5.35 | 4.28 | 60.87 | 5.18 | 4.30 |
| 56 | C$_{32}$H$_{30}$ClN$_2$O$_2$SNa · 0.8H$_2$O | 66.32 | 5.50 | 4.83 | 66.43 | 5.58 | 4.75 |
| 57 | C$_{31}$H$_{27}$F$_2$N$_2$O$_2$SNa · 1.5H$_2$O | 64.23 | 5.22 | 4.83 | 64.16 | 5.26 | 4.66 |
| 58 | C$_{35}$H$_{33}$F$_2$N$_2$O$_2$SNa · 2.5H$_2$O | 64.51 | 5.83 | 4.30 | 64.80 | 5.57 | — |
| 59 | C$_{30}$H$_{26}$F$_2$NO$_3$SNa · 1.7H$_2$O | 62.97 | 5.18 | 2.45 | 62.86 | 5.21 | 2.28 |
| 60 | C$_{32}$H$_{31}$F$_2$N$_2$OS$_2$Na· | 62.12 | 5.38 | 4.53 | 62.13 | 5.50 | 4.36 |

Assays for Determining Biological Activity

The leukotriene antagonist properties of the compounds of the present invention are evaluated using the following assays.

1. [$^3$H]LTD$_4$ Receptor Binding Assay in DMSO-differentiated U937 Cells (a human monocytic cell line);
2. [$^3$H]LTD$_4$ Receptor Binding on Guinea Pig Lung Membranes;
3. [$^3$H]LTD$_4$ Receptor Binding on Human Lung Membranes;
4. In Vitro Guinea Pig Trachea; and
5. In Vivo Assays in Anesthetized Guinea Pigs.

The above assays are described in T. R. Jones et al., Can. J. Physiol. Pharmacol., 1991,69, 1847–1854.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the inserted into one end of the box and coupled to a Grass volumetric pressure transducer (PT5-A) which is then connected to a Buxco Electronics preamplifier (Buxco Electronics Inc., Sharon, Conn.). The preamplifier is connected to a Beckman Type R Dynograph and to a s Buxco computer consisting of waveform analyzer, Data Acquisition Logger with Buxco software. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 post sensitization. In order to eliminate the serotonin component of the response, rats are pretreated intravenously 5 minutes prior to aerosol challenge with 3.0 µg/kg of methysergide. Rats are then exposed to an aerosol of 3% EA in saline for exactly 1 minute, then their respiratory profiles are recorded for a further 30 minutes. The duration of continuous dyspnea is measured by the Buxco computer.

Compounds are generally administered either orally 2–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. The activity of compounds is determined in terms of their ability to decrease the duration of antigen-induced dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65 HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or *Ascaris suum* antigen; 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., Prostaglandins, 28, 173–182 (1984), and McFarlane, C. S. et al., Agents Actions, 22, 63–68 (1987).)

Prevention of Induced Bronchoconstriction in Allergic Sheep

A. Rationale: Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods: Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.) and b) they have previously responded to inhalation challenge with *Ascaris suum* with both an acute bronchoconstriction and a late bronchial obstruction (W. M. Abraham et al., Am. Rev. Resp. Dis., 128,839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medical-nebulizer (Raindrop ®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is connected to the inspiratory pan of a Harvard respirator. The aerosol is delivered at a tidal volume of 500 mL of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5–1 hr prior to Ascaris challenge and for 8 hrs after Ascaris as described above.

Statistical Analysis: A Kruskal-Wallis one way ANOVA test is used to compare the acute immediate responses to antigen and the peak late response in the controls and the drug treated animals.

The invention will now be illustrated by the following non-limiting examples in which, unless stated otherwise:
(i) all operations were carried out at room or ambient temperature, that is, at a temperature in the range 18°–25° C.;
(ii) evaporation of solvent was carded out using a rotary evaporator under reduced pressure (600–4000 pascals: 4.5–30 mm. Hg) with a bath temperature of up to 60° C.;
(iii) the course of reactions was followed by thin layer chromatography (TLC) and reaction times are given for illustration only;
(iv) melting points are uncorrected and "d" indicates decomposition; the melting points given are those obtained for the materials prepared as described; polymorphism may result in isolation of materials with different melting points in some preparations;
(v) the structure and purity of all final products were assured by at least one of the following techniques: TLC, mass spectrometry, nuclear magnetic resonance (NMR) spectrometry, or microanalytical data;
(vi) yields are given for illustration only;
(vii) when given, NMR data are in the form of delta (δ) values for major diagnostic protons, given in pans per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.; in addition "Ar" signifies an aromatic signal;
(viii) chemical symbols have their usual meanings; the following abbreviations have also been used v (volume), w (weight), b.p. (boiling point), m.p. (melting point), L. (liter(s)), mL. (milliliters), g. (gram(s)), mg (milligram(s)), mol. (moles), mmol (millimoles), eq. (equivalent(s)).

EXAMPLE 2

(R)-1-(((3-(2-chlorophenyl)-1-(3-(2-(6,7-difluoro-2-quinolinyl)ethenyl)phenyl)propyl)thio)methyl)cyclopropaneacetic acid, sodium salt

Step 1

6,7-Difluoro-2-methylquinoline

Crotonaldehyde (226.34 g, 3.23 tool) in 100 mL of 2-butanol was added dropwise to a refluxing solution of 3,4-difluoroaniline (417.27 g, 3.23 tool), p-chloranil (794.65 g, 3.23 mol) and HCl conc. (808 mL) in 5.4 L of 2-butanol. After 2 hours of heating 2.7 L of solvent was removed under vacuum at ca. 60° C. Then 2 L of toluene was added to the reaction mixture followed by removal of 2.5–3 L of solvent until a very pasty solid formed. THF (2L) was added and the mixture heated 30 min. after which it was cooled to 0° C. The solid was collected and washed with THF until pure by tlc. The solid was then dissolved in aq. $K_2CO_3$/EtOAc and the organic phase separated. The aqueous phase was extracted with EtOAc (2X) and the organic phases combined, dried over $MgSO_4$, and the solvent removed. The product was crystallized in the minimum amount of EtOAc to give 328.08 g (57%) of the title compound.

$^1$H NMR (CD$_3$COCD$_3$): δ 8.19 (1H, d), 7.75 (2H, m), 7.4 (1H, d), 2.64 (3H, s).

Step 2

3-(2-(6,7-Difluoro-2-quinolinyl)ethenyl)benzaldehyde

A solution of isophthalaldehyde (312.4 g, 2.33 mmol), 6,7-difluoro-2-methylquinoline (278.4 g, 1.55 mmol) and acetic anhydride (416 mL) in 2 L of xylene was heated to reflux overnight. The solvent was evaporated and the product was swished in 2.5 L of EtOAc to yield the title compound (272 g, 56%). $^1$H NMR (CD$_3$COCD$_3$): δ 10.12 (1H, s), 8.4 (1H, d), 8.29 (1H, s), 8.1–7.85 (6H, m), 7.7–7.55 (2H, m).

Step 3

1-(3-(2-(6,7-Difluoro-2-quinolinyl)ethenyl)phenyl)-2-propen-1-ol

The aldehyde of Step 2 (35.93 g, 122 mmol) was suspended in 360 mL of toluene and cooled to 0° C. 1.0 M Vinylmagnesium bromide in THF (135 mL) was added into the addition funnel and the whole system was degassed by applying vacuum and flushed with nitrogen 3 times. The Grignard reagent was then added slowly at 0° C. and the mixture was stirred at 0° C. for 15 min. Cold 25% aq. NH$_4$OAc was then added and the product was extracted in hot toluene, washed with brine, and dried over Na$_2$SO$_4$. The cloudy solution was filtered through celite, concentrated, and filtered through silica with EtOAc: toluene 10:90 to afford 32.04 g (81%) of the title product.

¹H NMR (CD₃COCD₃): δ 8.32 (1H, d), 7.92-7.8 (4H, m), 7.75 (1H, br s), 7.6 (1H, m), 7.5-7.35 (3H, m), 6.05 (1H, ddd), 5.37 (1H, ddd), 5.25 (1H, m), 5.1 (1H, ddd), 4.61 (1H, d).

Step 4

3-(2-Chlorophenyl)-1-(3-(2-(6,7-difluoro-2-quinolinyl)ethenyl)phenyl)-1-propanone A mixture of the allylic alcohol of Step 3 (1.214 g, 3.75 mmol), 1-chloro-2-iodobenzene (480 FtL), Pd(OAc)₂ (30 mg), LiCl (194 mg), LiOAc.2H₂O (995 rag) and Bu₄NCI (2.13 g) in 7.5 mL of DMF was degassed under vacuum and heated to 100° C. under N₂ for 3 hr. 25% Aq. NH₄OAc was then added and the product was extracted in EtOAc, dried over Na₂SO₄, and purified by flash chromatography with EtOAc: toluene 2.5:97.5. Yield 1.53 g, 94%.

¹H NMR (CDCl₃) δ 8.22 (1H, s), 8.08 (1H, d), 7.93 (1H, d), 7.87-7.70 (3H, m), 7.63 (1H, d), 7.55-7.45 (2H, m), 7.43-7.28 (3H, m), 7.27-7.13 (2H, m), 3.38 (2H, t), 3.22 (2H, t).

Step 5

(S)-3-(2-Chlorophenyl)-1-(3-(2-(6,7-difluoro-2-quinolinyl)ethenyl)phenyl) propanol At −20° C., a solution of (−)-B-chlorodiisopinocampheylborane (1.74 g, 1.5 equiv.) in 9 mL of CH₂Cl₂ was added dropwise to a suspension of the ketone of Step 4 (1.52 g, 3.5 mmol) in 18 mL of CH₂Cl₂ and the mixture was stirred at 0° C. for an hour and at room temperature for 2 hours. At 0° C., 10% aq. diethanolamine was added and the mixture was stirred at r.t. for 30 min. The product was extracted in EtOAc:THF 1:1, washed with brine, dried over Na₂SO₄, and concentrated. The oil was dissolved in ether and conc. HCl (5 ml) was added. The precipitated hydrochloride was filtered, washed with ether, and dissolved in THF:0.1 N NaOH. The product was extracted in EtOAc:THF 1:1, washed with brine, dried over Na₂SO₄ and purified by flash chromatography with EtOAc:toluene 10:90. Yield 1.125 g, 74%.

¹H NMR (CD₃COCD₃—D₃SOCD₃) δ 8.37 (1H, d), 7.97-7.83 (4H, m), 7.78 (1H, s), 7.61 (1H, m), 7.47 (1H, d), 7.44-7.32 (4H, m), 7.30-7.16 (2H, m), 5.25 (1H, d, OH), 4.73 (1H br t), 2.92 (1H, m), 2.78 (1H, m), 2.00 (2H, m).

Step 6

1.1-Cyclopropanedimethanol cyclic sulfite

To a solution of BH₃:THF complex (1M in THF, 262 mL) was added diethyl 1,1-cyclopropanedicarboxylate (25 g, 134 mmol) at 25° C. under N₂. The solution was heated at reflux for 6 hours, cooled to room temperature, and MeOH (300 mL) was cautiously added. The solution was stirred for 1 hour and then concentrated to an oil. The crude diol was dissolved in CH₂Cl₂ (234 mL) and SOCl₂ (15.9 g, 134 mmol) was added dropwise over a period of 15 min at 25° C. After stirring for another 15 min, the mixture was washed with aqueous NaHCO₃. The organic extract was dried over Na₂SO₄, filtered, and concentrated to give quantitatively the title compound as a white solid.

Step 7

1-(Hydroxymethyl)cyclopropaneacetonitrile

To a solution of the cyclic sulfite product of Step 6 (14.7 g, 199 mmol) in DMF (83 mL) was added NaCN (9.74 g, 199 mmol). The mixture was heated to 90° C. for 20 hours. Upon cooling, EtOAc (400 mL) was added and the solution was washed with saturated NaHCO₃ solution (55 mL), H₂O (4×55 mL), saturated CaCl solution, and dried over Na₂SO₄. The solution was concentrated to give 7.1 g (65 %) of the title compound.

Step 8

1-(Acetylthiomethyl)cyclopropaneacetonitrile

To a solution of the alcohol of Step 7 (42 g, 378 mmol) in dry CH₂Cl₂ (450 mL) at −30° C. was added Et₃N (103.7 mL, 741 mmol) followed by CH₃SO₂Cl (43.3 mL, 562 mmol) dropwise. The mixture was warmed to 25° C., washed with NaHCO₃, dried over Na₂SO₄, and concentrated in vacuo to give the corresponding mesylate. The mesylate was then dissolved in DMF (450 mL) and cooled to 0° C. Potassium thioacetate (55.4 g, 485 mmol) was added, and the mixture was stirred at 25° C. for 18 hours. EtOAc (1.5 L) was added, the solution was washed with NaHCO₃, dried over Na₂SO₄, and concentrated in vacuo to give 45 g (70%) of the title compound.

Step 9

Methyl 1-(mercaptomethyl)cyclopropaneacetate

To a solution of the nitrile of Step 8 (45 g, 266 mmol) in MeOH (1.36 L) was added H₂O (84 mL) and conc. H₂SO₄ (168 mL). The mixture was heated to reflux for 20 hours, cooled to 25° C., H₂O (1 L) was added and the product was extracted with CH₂Cl₂ (2×1.5 L). The organic extract was washed with H₂O and dried over Na₂SO₄. Concentration of the organic solution gave 36 g (93%) of the title compound.

Step 10

Methyl (R)-1-(((3-(2-chlorophenyl))-1-(3-(2-(6,7-difluoro-2-quinolinyl)ethenyl)phenyl)propyl)thio)methyl)cyclopropaneacetate At −40° C., triethylamine (430 μL, 1.5 equiv.) and methanesulfonyl chloride (190 μL, 1.2 equiv.) were added to a solution of the alcohol of Step 5 (895 mg, 2.05 mmol) in 35 mL of anh. THF and the mixture was stirred at −40° C. for 30 min. and at 0° C. for an hour. It was then poured into saturated aq. NaHCO₃. The mesylate was extracted in EtOAc, washed with brine, dried over Na₂SO₄, and stripped with toluene twice.

At room temperature, the thiol of Step 9 (359 mg, 1.1 equiv.) was added to a degassed suspension of anh. Cs₂CO₃ (1.44 g, 2 equiv.) in 3 mL of anh. CH₃CN. Then, a solution of the mesylate in 7 mL of anh. CH₃CN was added and the mixture was stirred at room temperature for 5 hours. It was added to 25% aq. NH₄OAc and the title product was extracted in EtOAc, dried over Na₂SO₄, and purified by flash chromatography on silica with EtOAc:toluene 5:95.

¹H NMR (CDCl₃) 15 8.08(1H, d), 7.82 (1H, dd), 7.75-7.57 (3H, m), 7.51 (2H, m), 7.41-7.27 (4H, m), 7.19-7.09 (3H, m), 3.87 (1H, t), 3.62 (3H, s), 2.88-2.67 (2H, m), 2.50 (2H, m), 2.39 (2H, m), 2.20 (2H, m) 0.55-0.35 (4H, m).

Step 11

A mixture of the product of Step 10 (477 mg, 825 mmol), 10N NaOH (480 μL), H₂O (2 mL), MeOH (4 mL), and THF (8 mL) was degassed and stirred at room temperature overnight. 25% Aq. NH$_4$OAc was then added and the title acid was extracted in EtOAc, dried over Na$_2$SO$_4$, and purified by flash chromatography with EtOAc:toluene: AcOH 5:95:1. Yield 414 mg, 89%.

The title sodium salt was formed in EtOH by addition of 1.0 equiv. of 1N NaOH and was freeze-dried.

Anal. calcd for C$_{32}$H$_{27}$ClF$_2$NO$_2$SNa.2.4 H$_2$O: C, 61.08; H, 5.09; N, 2.23. Found: C, 61.03; H, 5.17; N, 2.20.

EXAMPLE 3

(R)-1-(((3-(2-Bromophenyl)-1-(3-(2-(6,7-difluoro-2-quinolinyl)ethenyl)phenyl)propyl)thio)metyl)cyclopropaneacetic acid, sodium salt

Step 1

3-(Hydroxymethyl)benzaldehyde

To isophthalaldehyde (200 g) in absolute ethanol (3 L) at 0° C. was added NaBH$_4$ (15.6 g). After 1 hour at 0° C. the reaction mixture was poured onto 25% aqueous ammonium acetate (2 L). The ethanol was evaporated and the product was extracted with EtOAc. The resulting mixture was purified by flash chromatography (30% EtOAc/Hexane) to provide 94 g of the title product.

Step 2

3-(((2-Tetrahydropyranyl)oxy)methyl)benzaldehyde

To the alcohol of Step 1 (94 g) in CH$_2$Cl$_2$ (1.5 L) at 0° C. was added 3,4-dihydro-2H-pyran (300 mL) followed by pyridinium p-toluenesulfonate (5.0 g). After 3 hours at room temperature, the reaction mixture was poured on aqueous 25% ammonium acetate and extracted with CH$_2$Cl$_2$. The resulting mixture was purified by flash chromatography (50% EtOAc in toluene) to give 147 g of the title aldehyde.

Step 3

1-(3-(((2-Tetrahydropyranyl)oxy)methyl)phenyl)-2-propen-1-ol

Using the procedure of Example 2, Step 3, 48.91 g of the aldehyde of Step 2 was converted to 39.66 g (72%) of the title alcohol.

$^1$H NMR (CDCl$_3$) δ 7.40–7.25 (4H, m), 6.07 (1H, m), 5.38 (1H, d), 5.21 (2H, br d), 4.80 (1H, d), 4.72 (1H, t), 4.50 (1H, d), 3.94 (1H, m), 3.57 (1H, m), 1.99 (1H, d, OH), 1.95–1.48 (6H, m).

Step 4

3-(2-Bromophenyl)-1-(3-(((2-tetrahydropyranyl)oxy)methyl)phenyl)-1-propanone

A mixture of the allylic alcohol of Step 3 (30.14 g, 121 mmol), 1,2-dibromobenzene (16 mL), Pd(OAc)$_2$ (830 mg), LiCl (5.38 g), LiOAc.2H$_2$O (31.6 g), and Bu$_4$NCl (67.96 g) in 240 mL of DMF was degassed and heated to 85° C. under N$_2$ for 30 min and at 90° C. for 45 min. It was then added to ice and 25% aq. NH$_4$OAc (2 L). The title ketone was extracted in EtOAc, dried over Na$_2$SO$_4$, and purified by flash chromotography on silica with EtOAc:hexane 10:90. Yield 29.53, 60%

$^1$H NMR (CDCl$_3$) δ 7.97 (1H, s), 7.90 (1H, d), 7.57 (2H, t), 7.45 (1H, t), 7.32 (1H, dd), 7.24 (1H, dd), 7.09 (1H, m), 4.83 (1H, d), 4.74 (1H, t), 4.55 (1H, d), 3.92 (1H, m), 3.58 (1H, m), 3.32 (2H, m), 3.20 (2H, m), 1.95–1.45 (6H, m).

Step 5

(S)-3-(2-Bromophenyl)-1-(3-(((2-tetrahydropyranyl)oxy)methyl)phenyl)-1-propanol

To a solution of the ketone of Step 4 (29.00 g, 72 mmol) in 260 mL of anh. THF at -55° C. (temperature of the reaction mixture) was added dropwise a solution of (R)-tetrahydro-1-methyl-3,3-diphenylI 1H,3H-pyrrolo[1,2-c][1,3,2¦oxazaborole, borane complex (J. Org. Chem., 56, 751 (1991)) (4.07 g, 0.2 equiv.) in 70 mL of THF, followed by 1.0M borane in THF (75 mL). The mixture was then allowed to warm to −20° C. over 3 hr. It was then cooled to −45° C., quenched with 10% aq. diethanolamine, and warmed to room temperature. 25% Aq. NH$_4$OAc was then added and the chiral alcohol was extracted in EtOAc, dried over Na$_2$SO$_4$ and filtered through silica with EtOAc: toluene 5:95 to 10:90. Yield 27.52g, 94%.

$^1$H NMR (CDCl$_3$) δ 7.53 (1H, d), 7.40–7.16 (6H, m), 7.05 (1H, m), 4.80 (1H, d), 4.72 (2H, m), 4.50 (1H, d), 3.93 (1H, m), 3.55 (1H, m), 2.90 (1H, m), 2.80 (1H, m), 2.08 (2H, m), 1.95 (1H, d, OH), 1.90–1.48 (6H, m).

Step 6

Methyl (R)-1-(((3-(2-bromophenyl)-1-(3-(((2-tetrahydropyranyl)oxy)methyl)phenyl)propyl)thio)methyl)cyclopropaneacetate At −40° C., triethylamine (9.2 mL, 1.3 equiv.) and methanesulfonyl chloride (4.3 mL, 1.1 equiv.) were added to a solution of the alcohol of Step 5 (20.55 g, 50.7 mmol) in 500 mL of CH$_2$Cl$_2$ and the mixture was allowed to warm to −20° C. over 30 min and was stirred at 0° C. for 1 hr. Saturated NaHCO$_3$ was added and the mesylate was extracted in CH$_2$Cl$_2$, dried over Na$_2$SO$_4$, and stripped with toluene twice.

At 0° C., Cs$_2$CO$_3$ (27.02 g, 1.6 equiv.) was added to a degassed solution of methyl 1-(mercaptomethyl)cyclopropaneacetate (9.09 g, 1.1 eq.; Example 2, Step 9) and the mesylate in 250 mL of anh. CH$_3$CN. The mixture was then agitated strongly at room temperature for 3 hr. and quenched at 0° C. by addition of 25% aq. NH$_4$OAc. The title thioether was extracted in EtOAc, washed with brine, dried over Na$_2$SO$_4$, and purified by filtration through silica with EtOAc:toluene 2.5:97.5. Yield 22.64 g, 77%.

$^1$H NMR (CDCl$_3$) δ 7.50 (1H, d), 7.34–7.13 (6H, m), 7.04 (1H, m), 4.79 (1H, d), 4.72 (1H, t), 4.52 (1H, d), 3.93 (1H, m), 3.83 (1H, t), 3.62 (3H, s), 3.56 (1H, m), 2.72 (2H, m), 2.42 (4H, m), 2.15 (2H, m), 1.93–1.50 (6H, m), 0.51–0.33 (4H, m).

Step 7

Methyl (R)-1-(((3-(2-bromophenyl)-1-(3-(hydroxymethyl)phenyl)propyl)thio)methyl)cyclopropaneacetate A solution of the tetrahydropyranyl ether of Step 6 (1.552 g, 2.83 mmol) and pyridinium p-toluenesulfonate (176 mg, 0.25 equiv.) in 15 mL of MeOH was stirred at room temperature for 2 days. Triethylamine (100 μL, 1 equiv.) was then added, the solvent evaporated, and the residue purified by flash chromotography on silica with EtOAc:toluene 20:80. Yield 1.189 g, 91%.

$^1$H NMR (CDCl$_3$) δ 7.50 (1H, d), 7.39 (1H, s), 7.36–7.14 (5H, m), 7.05 (1H, m), 4.70 (2H, d), 3.73 (1H, t), 3.60 (3H, s), 2.80 (1H, m), 2.70 (1H, m), 2.45 (3H, m), 2.26 (1H, d), 2.16 (2H, m), 2.05 (1H, t, OH), 0.50–0.35 (4H, m).

Step 8

Methyl (R)-1-(((3-(2-bromophenyl)-1-(3-formylphenyl)propyl)-thio)methyl)cyclopropaneacetate A mixture of the benzylic alcohol of Step 7 (1.176 g, 2.54 mmol) and activated $MnO_2$ (4.6 g, 20 equiv.) in 25 mL of EtOAc was stirred at room temperature for 4 hr. Another batch of $MnO_2$ (1.1 g) was added and the mixture was stirred 20 min. It was filtered through celite to afford 1.014 g (87%) of the title aldehyde.

$^1H$ NMR ($CDCl_3$) δ 10.02 (1H, s), 7.85 (1H, s), 7.78 (1H, d), 7.67 (1H, d), 7.52 (2H, 2d), 7.26–7.14 (2H, m), 7.05 (1H, m), 3.90 (1H, t), 3.60 (3H, s), 2.82 (1H, m), 2.68 (1H, m), 2.45 (2H, m), 2.35 (2H, m), 2.18 (2H, m), 0.55–0.33 (4H, m).

Step 9

((6,7-Difluoro-2-quinolinyl)methyl)triphenylphosphonium bromide 6,7-difluoro-2-methylquinoline (Example 2, Step 1) was heated to reflux in $CCl_4$ with 1.0 equiv. of N-bromosuccinimide and 0.005 equiv. of benzoyl peroxide under a sun lamp to give the bromomethyl derivative. This bromide was then treated with triphenylphosphine in refluxing acetonitrile to give the title compound.

Step 10

Methyl (R)-1-(((3-(2-bromophenyl)-1-(3-(2-(6,7-difluoro-2-quinolinyl)ethenyl)phenyl)propyl)thio)methyl)cyclopropaneacetate At −78° C., 1.6M BuLi in hexane (700 µL) was added to a suspension of the phosphonium salt of Step 9 (646 mg, 1.1 equiv.) in 6 mL of anh. THF and the mixture was stirred at −10° C. for 10 min. At −78° C., a solution of the aldehyde of Step 8 (515 mg, 1.12 mmol) in 4 mL of THF was then added dropwise. The mixture was stirred at −78° C. for 30 min. and at −10° C. for 30 min. and was quenched with 25% aq. $NH_4OAc$. The product was extracted in EtOAc, dried over $Na_2SO_4$, is and purified by flash chromatography on silica with EtOAc:toluene 2.5:97.5 and 5:95.

$^1H$ NMR ($CDCl_3$) δ 8.08 (1H, d), 7.83 (1H, dd), 7.75–7.60 (3H, m), 7.52 (3H, m), 7.40–7.30 (3H, m), 7.25–7.15 (2H, m), 7.05 (1H, m), 3.88 (1H, t), 3.61 (3H, s), 2.90–2.78 (1H, m), 2.78–2.66 (1H, m), 2.50 (2H, m), 2.41 (2H, m), 2.19 (2H, m), 0.55–0.25 (4H, m).

Step 11

A mixture of the product of Step 10 (363 mg, 583 mmol), 10N NaOH (400 µL), $H_2O$ (1.6 mL), MeOH (3.2 mL) and THF (6.4 mL) was degassed and stirred at room temperature overnight. 25% Aq. $NH_4OAc$ was then added and the title acid was extracted in EtOAc, dried over $Na_2SO_4$, and purified by flash chromatography with EtOAc:toluene:AcOH 7.5:92.5:1. Yield 307 mg, 87%.

The title sodium salt was formed in EtOH by addition of 1.0 equiv. of 1N NaOH and was freeze-dried.

Anal. calcd for $C_{32}H_{27}BrF_2NO_2SNa.1.2H_2O$: C, 58.98; H, 4.54; N, 2.15. Found: C, 58.98, H, 4.65; N, 1.98.

EXAMPLES 1, 6, 7, 8, 9

Using the procedure of Example 2, but substituting 1-chloro-2-iodobenzene for the appropriate halobromobenzene or haloiodobenzene in Step 4, the compounds of Examples 1 and 6–9 were prepared.

EXAMPLE 28

(R)-1-(((1-(3-(2-(6,7-Difluoro-2-quinolinyl)ethenyl)-phenyl)-3-phenylpropyl)thio)methyl)cyclopropane acid, sodium salt

Step 1

(R)-1-(((3-(2-Bromophenyl)-1-(3-(((2-tetrahydropyranyl)oxy)methyl)phenyl)propyl)thio)methyl)cyclopropaneacetic acid Using the procedure of Example 2, Step 11, the ester of Example 3 Step 6 was hydrolyzed to the title acid.

Step 2

Methyl (R)-1-(((1-(3-(((2-Tetrahydropyranyl)oxy)methyl)-phenyl)-3-phenylpropyl)thio)methyl)cyclopropaneacetate To a THF solution (25 mL) of the bromide of Step 1 (2.0 g) at −100° C. was added dropwise 1.6M n-BuLi (5.15 mL). After 30 min. at −78° C., the reaction mixture was poured on 25% aq. solution of $NH_4OAc$, extracted with EtOAc, and dried over $Na_2SO_4$. The resulting mixture was then purified by flash chromatography with EtOAc:hexane 1:1 to afford 1.0 g of the desbromo product. The acid was esterified with $CH_2N_2$ in ether.

$^1H$ NMR ($CD_3COCD_3$) δ 7.38–7.18 (9H, m), 4.70 (1H, m), 4.60 (2H, ab), 3.85 (2H, m), 3.58 (3H, s), 3.50 (1H, m), 2.65 (2H, m), 2.45 (2H, s), 2.35 (2H, ab), 2.25–2.08 (2H, m), 1.90–1.45 (6H, m), 0.50–0.30 (4H, m).

Step 3

Using the procedure of Example 3, Steps 7–11, the product of Step 2 was converted to the title sodium salt.

Anal. calcd. for $C_{32}H_{28}F_2NO_2SNa.1.5 H_2O$: C, 66.43; H, 5.62; N, 2.42. Found: C, 66.25; H, 5.27; N, 2.34.

What is claimed is:

1. A compound of the Formula I:

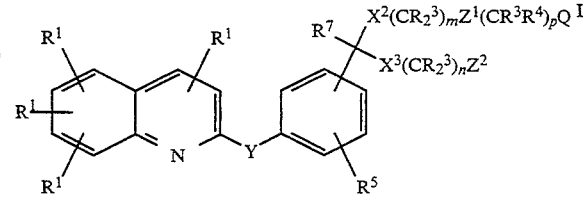

wherein:

$R^1$ is H, halogen, —$CF_3$, —CN, —$NO_2$, or —$N_3$;

$R^2$ is lower alkyl, lower alkenyl, lower alkynyl, —$CF_3$, —$CH_2F$, —$CHF_2$, $Ph(R^{25})_2$, $CH_2Ph(R^{25})_2$, or $CH_2CH_2Ph(R^{25})_2$, or two $R^2$ groups joined to the same atom may form a saturated carboxylic ring of up to 8 members;

$R^3$ is H or $R^2$;

$R^4$ is $R^3$, halogen, —$NO_2$, —CN, —$CF_3$, —$OR^3$, $N(R^3)_2$, $NR^3COR^7$, —$SR^2$, $S(O)R^2$, $S(O)_2R^2$, $CHR^7OR^3$, or $CHR^7SR^2$;

$CR^3R^4$ may be the radical of a standard amino acid;

$R^5$ is H, halogen, —NO$_2$, —N$_3$, —CN, —SR$^2$,—S-(O)R$^2$, S(O)$_2$R$^2$, —N(R$^{12}$)$_2$, —OR$^3$, —COR$^3$, or lower alkyl;

$R^6$ is —(CH$_2$)$_s$—C(R$^7$)$_2$—(CH$_2$)$_s$—R$^8$ or —CH$_2$CON(R$^{20}$)$_2$;

$R^7$ is H or lower alkyl;

$R^8$ is B) the radical W—R$^9$;

$R^9$ contains up to 21 carbon atoms and is (1) a hydrocarbon radical or (2) an acyl radical of an organic acyclic or monocyclic carboxylic acid containing not more than 1 heteroatom in the ring;

$R^{10}$ is H, lower alkyl, or halogen;

$R^{11}$ is lower alkyl, —COR$^{14}$, ph(R$^{25}$)$_2$, CH$_2$Ph(R$^{25}$)$_2$, or CH$_2$CH$_2$Ph(R$^{25}$)$_2$;

$R^{12}$ is H or R$^{11}$;

$R^{13}$ is lower alkyl, lower alkenyl, lower alkynyl, —CF$_3$, Ph(R$^{25}$)$_2$, CH$_2$Ph(R$^{25}$)$_2$, or CH$_2$CH$_2$Ph(R$^{25}$)$_2$;

$R^{14}$ is H or R$^{13}$;

$R^{16}$ is H, lower alkyl, or OH;

$R^{17}$ is lower alkyl, lower alkenyl, lower alkynyl, Ph(R$^{25}$)$_2$, CH$_2$Ph(R$^{25}$)$_2$, or CH$_2$CH$_2$Ph(R$^{25}$)$_2$;

$R^{18}$ is R$^{13}$;

$R^{19}$ is H, lower alkyl, lower alkenyl, lower alkynyl, —CF$_3$, Ph, CH$_2$Ph, or CH$_2$CH$_2$Ph;

$R^{20}$ is H, lower alkyl, Ph(R$^{25}$)$_2$, CH$_2$Ph(R$^{25}$)$_2$, or CH$_2$CH$_2$Ph(R$^{25}$)$_2$;

$R^{21}$ is H or R$^{17}$;

$R^{22}$, $R^{23}$, and $R^{24}$ is each independently H, lower alkyl, CF$_3$, CF$_2$H, CH$_2$CF$_3$, halogen, OR$^3$, SR$^2$, or an electron pair;

$R^{25}$ is H, —CO$_2$R$^7$,—COR$^7$,—CN, CF$_3$, NO$_2$, SCF$_3$, lower alkyl, —SR$^{26}$,—OR$^{27}$, N(R$^{27}$)$_2$, CON(R$^{27}$)$_2$, or halogen.

$R^{26}$ is lower alkyl, phenyl, or benzyl;

$R^{27}$ is R$^{26}$, H, or COR$^7$;

m, n, and p is each independently 0–8;

m+p is 1–10 when X$^2$ is O, S, S(O), or S(O)$_2$ and Z$_1$ is a bond;

n+p is 0–10 when Z$_1$ is HET (R$^{22}$R$^{23}$R$^{24}$);

m+p is 0–10 when X$^2$ is CR$^3$R$^{16}$;

s is 0–3;

Q is tetrazol-5-yl, —CO$_2$R$^3$, —CO$_2$R$^6$, —CONHS(O)$_2$R$^{13}$, —CN, —CON(R$^{20}$)$_2$, —NR$^{21}$S(O)$_2$R$^{13}$, —NR$^{21}$CON(R$^{20}$)$_2$, —NR$^{21}$COR$^{14}$, OCON(R$^{20}$)$_2$, —COR$^{19}$, —S(O)R$^{18}$, —S(O)$_2$R$^{18}$, —S(O)$_2$N(R$^{20}$)$_2$, —NO$_2$, NR$^{21}$CO$_2$R$^{17}$, —C(N(R$^{20}$)$_2$)=NR$^{21}$, —C(R$^{19}$)=NOH, or —C(R$^3$)$_2$OH;

W is S or NR$^3$;

X$^1$ is —NR$^3$, —C(R$^3$)$_2$—, or a bond;

X$^2$ and X$^3$ is each independently O, S, S(O), S(O)$_2$, CR$^3$R$^{16}$, or a bond;

Y is —CR$^3$=CR$^3$—, —C(R$^3$)$_2$—X$^1$—, —X$^1$—C(R$^3$)$_2$—, —C(R$^3$)$_2$—X$^1$—C(R$^3$)$_2$—, —C≡CO—, —CO—, —NR$^3$CO—, —CONR$^3$—, NR$^3$, or

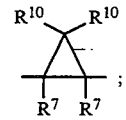

Z$_1$ is a bond;

Z$_2$ is benzylene or a heterocyclic moiety derived from pyridine, furan, thiophene, thiazole, pyrazine, benzimidazole, quinoline, benzothiazole, 5,6,7,8-tetrahydroquinoline, or 1,2,5-thiadiazole;

or a pharmaceutically acceptable salt thereof.

2. A compound of claim 1 of the Formula Ia:

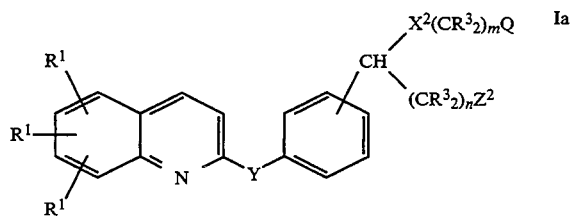

wherein:

R$^1$ is H, halogen, —CF$_3$;

m and n is each independently 1–6:

Q is CO$_2$R$^3$, CO$_2$R$^6$, —CONHS(O)$_2$R$^{13}$, tetrazol-5-yl, or C(R$^3$)$_2$OH;

X$^2$ is S or O;

Y is —CH=CH—, —CH$_2$—CH$_2$, —C≡C—, or —CH(CH$_2$)CH—;

Z$_2$ is HET (R$^{22}$R$^{23}$); and

HET is benzene, thiophene, or pyridine;

3. A compound of claim 1 of the Formula Ib:

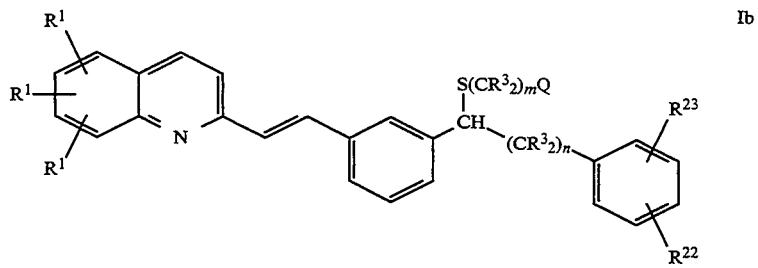

wherein:

R$^1$ is H, halogen or CF$_3$;

R$^3$ is H or lower alkyl, or two R$^3$ joined to the same carbon may form a carboxylic ring from 3 to 6 members;

R$^{22}$ and R$^{23}$ is each independently H, halogen, or lower alkyl;

m and n is each independently 1–5; and

Q is —CO$_2$R$^3$, tetrazol-5-yl, or —CONHS(O)$_2$R$^{13}$.

4. A compound of claim 1 of the Formula Ic:

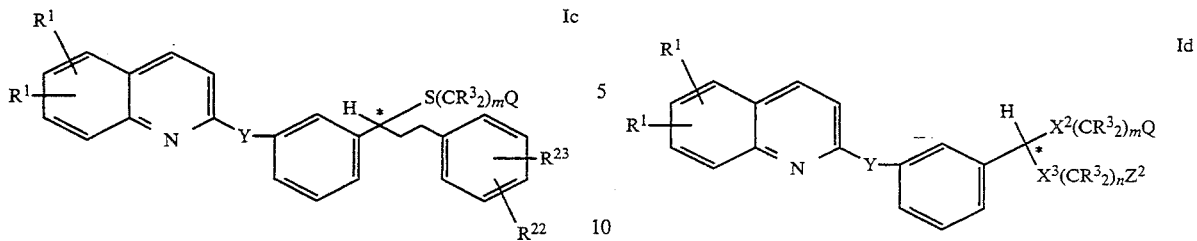

5. A compound of claim 1 of the Formula Id:

wherein the substituents are as follows:

wherein the substituents are as follows:

| Ex. | $R^1, R^1$ | Y | $(CR^3{}_2)mQ$ | $R^{22}, R^{23}$ | * |
|---|---|---|---|---|---|
| 1 | 6,7-$F_2$ | —CH=CH— | $CH_2$(1,1-c-Pr)$CH_2CO_2H$ | 2-F,H | (R) |
| 2 | 6,7-$F_2$ | —CH=CH— | $CH_2$(1,1-c-Pr)$CH_2CO_2H$ | 2-Cl,H | (R) |
| 3 | 6,7-$F_2$ | —CH=CH— | $CH_2$(1,1-c-Pr)$CH_2CO_2H$ | 2-Br,H | (R) |
| 4 | 6,7-$F_2$ | —CH=CH— | $CH_2$(1,1-c-Pr)$CH_2CO_2H$ | 3-F,H | rac |
| 5 | 6,7-$F_2$ | —CH=CH— | $CH_2$(1,1-c-Pr)$CH_2CO_2H$ | 3-Cl,H | rac |
| 6 | 6,7-$F_2$ | —CH=CH— | $CH_2$(1,1-c-Pr)$CH_2CO_2H$ | 3-Br,H | (R) |
| 7 | 6,7-$F_2$ | —CH=CH— | $CH_2$(1,1-c-Pr)$CH_2CO_2H$ | 4-F,H | (R) |
| 8 | 6,7-$F_2$ | —CH=CH— | $CH_2$(1,1-c-Pr)$CH_2CO_2H$ | 4-Cl,H | (R) |
| 9 | 6,7-$F_2$ | —CH=CH— | $CH_2$(1,1-c-Pr)$CH_2CO_2H$ | 4-Br,H | (R) |
| 10 | 6,8-$F_2$ | —$CH_2$—$CH_2$— | $CH_2C(CH_3)_2CH_2CO_2H$ | 4-Br,H | rac |
| 11 | 6,8-$F_2$ | —$CH_2$—$CH_2$— | $CH_2C(CH_3)_2CH_2CO_2H$ | 4-Br,H | rac |
| 12 | 6,8-$F_2$ | —$CH_2$—$CH_2$— | $CH_2C(CH_3)_2CH_2CO_2H$ | 4-Br,H | rac |
| 13 | 6,8-$F_2$ | —$CH_2$—$CH_2$— | $CH_2C(CH_3)_2CH_2CO_2H$ | 4-Br,H | rac |
| 14 | 6,8-$F_2$ | —$CH_2$—$CH_2$— | $CH_2C(CH_3)_2CH_2CO_2H$ | 4-Br,H | rac |
| 15 | 6,8-$F_2$ | —$CH_2$—$CH_2$— | $CH_2C(CH_3)_2CH_2CO_2H$ | 4-Br,H | rac |
| 16 | 6,8-$F_2$ | —$CH_2$—$CH_2$— | $CH_2C(CH_3)_2CH_2CO_2H$ | 4-Br,H | rac |
| 17 | 6,8-$F_2$ | —$CH_2$—$CH_2$— | $CH_2C(CH_3)_2CH_2CO_2H$ | 4-Br,H | rac |
| 18 | 6,8-$F_2$ | —$CH_2$—$CH_2$— | $CH_2C(CH_3)_2CH_2CO_2H$ | 4-Br,H | rac |
| 19 | 6,7-$F_2$ | —C≡C— | (1,1-c-Pr)$CH_2CO_2H$ | 4-Br,H | rac |
| 20 | 6,7-$F_2$ | —C≡C— | (1,1-c-Pr)$CH_2CO_2H$ | 4-Br,H | rac |
| 21 | 6,7-$F_2$ | —C≡C— | (1,1-c-Pr)$CH_2CO_2H$ | 4-Br,H | rac |
| 22 | 6,7-$F_2$ | —C≡C— | (1,1-c-Pr)$CH_2CO_2H$ | 4-Br,H | rac |
| 23 | 6,7-$F_2$ | —C≡C— | (1,1-c-Pr)$CH_2CO_2H$ | 4-Br,H | rac |
| 24 | 6,7-$F_2$ | —C≡C— | (1,1-c-Pr)$CH_2CO_2H$ | 4-Br,H | rac |
| 25 | 6,7-$F_2$ | —C≡C— | (1,1-c-Pr)$CH_2CO_2H$ | 4-Br,H | rac |
| 26 | 6,7-$F_2$ | —C≡C— | (1,1-c-Pr)$CH_2CO_2H$ | 4-Br,H | rac |
| 27 | 6,7-$F_2$ | —C≡C— | (1,1-c-Pr)$CH_2CO_2H$ | 4-Br,H | rac |
| 28 | 6,7-$F_2$ | —CH=CH— | $CH_2$(1,1-c-Pr)$CH_2CO_2H$ | H,H | (R) |
| 29 | 7-Cl,H | —CH=CH— | $CH_2$(1,1-c-Pr)$CH_2CO_2H$ | H,H | rac |
| 30 | 6,7-$Cl_2$ | —CH=CH— | $CH_2$(1,1-c-Pr)$CH_2CO_2H$ | 2-F, 4-$CH_3$ | rac |
| 31 | 6-F,H | —CH=CH— | $CH_2$(1,1-c-Pr)$CH_2CO_2H$ | 2-c-Pr, 4-F | rac |
| 32 | 6-Cl,H | —CH=CH— | $CH_2$(1,1-c-Pr)$CH_2CO_2H$ | 4-O-c-Pr,H | rac |
| 33 | 7-F,H | —CH=CH— | $CH_2$(1,1-c-Pr)$CH_2CO_2H$ | 2-O-c-Pr, 4-F | rac |
| 34 | 7-F,H | —CH=CH— | $CH_2$(1,1-c-Pr)$CH_2CO_2H$ | 2-F, 4-O-c-Pr | rac |
| 35 | 7-F,H | —CH=CH— | $CH_2$(1,1-c-Pr)$CH_2CO_2H$ | 2-F, 4-c-Pr | rac |
| 36 | 6-$CF_3$,H | —CH=CH— | $CH_2$(1,1-c-Pr)$CH_2CO_2H$ | 2-c-Pr, 4-Cl | rac |
| 37 | 6,7-$Cl_2$ | —CH=CH— | $CH_2$(1,1-c-Pr)$CH_2CO_2H$ | 2-$CF_3$,H | rac |
| 38 | 7-$CF_3$,H | —CH=CH— | $CH_2$(1,1-c-Pr)$CH_2CO_2H$ | 2-$CF_2$H, 4-O-c-Pr | rac |

| EX. | $R^1, R^1$ | Y | $X^2(CR^3{}_2)mQ$ | $X^3(C(R^3)_2)nZ^2$ | * |
|---|---|---|---|---|---|
| 39 | 7-Cl,H | —CH=CH— | $SCH_2C(S)H(Me)CO_2H$ | $CH_2CH_2$-3-Py | (S) |
| 40 | 7-Cl,H | —CH=CH— | $SCH_2C(Me)_2CH_2CO_2H$ | $CH_2CH_2$-3-Py | (R) |
| 41 | 7-Cl,H | —$CH_2CH_2$— | $SC(S)H(Me)CH_2CO_2H$ | $CH_2CH_2$-3-Py | (R) |
| 42 | 7-Cl,H | —$CH_2CH_2$— | $CH_2CH_2C(Me)_2CH_2CO_2H$ | $SCH_2$-2-Py | (S) |
| 43 | 7-Cl,H | —$CH_2CH_2$— | $CH_2CH_2C(Me)_2CH_2CO_2H$ | S-$CH_2CH_2$-2-Py | (S) |
| 44 | 7-Cl,H | —$CH_2CH_2$— | $SC(Me)_2CH_2CO_2H$ | $CH_2CH_2$-2-Py | (R) |
| 45 | 7-Cl,H | —$CH_2CH_2$— | $SCH_2$(1,1-c-Pr)$CH_2CO_2H$ | $CH_2CH_2$-2-Py | (R) |
| 46 | 7-Cl,H | —$CH_2CH_2$— | $SCH_2$(1,1-c-Pr)$CH_2CO_2H$ | $CH_2CH_2$-3-Py | (R) |
| 47 | 7-Cl,H | —$CH_2CH_2$— | $SCH_2$(1,1-c-Pr)$CH_2CO_2H$ | $CH_2CH_2CH_2$-3-Py | (R) |
| 48 | 7-Cl,H | —$CH_2CH_2$— | $CH_2CH_2$(1,2-(4-Cl-Phe))$CH_2CO_2H$ | $SCH_2CH_2$-2-Py | (R) |
| 49 | 7-Cl,H | —$CH_2CH_2$— | $SCH_2$(1,1-c-Pr)$CH_2CO_2H$ | $CH_2CH_2$-2-(5-Br-Py) | (R) |
| 50 | 7-Cl,H | —$CH_2CH_2$— | $SCH_2$(1,1-c-Pr)$CH_2CO_2H$ | $CH_2CH$-2-Pz | rac |
| 51 | 7-Cl,H | —$CH_2CH_2$— | $SCH_2$(1,1-c-Pr)$CH_2CO_2H$ | $CH_2CH_2$-2-(4-Me-Thz) | (R) |
| 52 | 7-Cl,H | —$CH_2CH_2$— | $SCH_2$(1,1-c-Pr)$CH_2CO_2H$ | $CH_2CH_2$-2-Qn | (R) |
| 53 | 7-Cl,H | —$CH_2CH_2$— | $SCH_2$(1,1-c-Pr)$CH_2CO_2H$ | $CH_2CH_2$-2-(7-Cl-Qn) | (R) |
| 54 | 7-Cl,H | —$CH_2CH_2$— | $CH_2CH_2$(1-2-Phe)$CH_2CO_2H$ | S-2-Bmz | (S) |
| 55 | 7-Cl,H | —$CH_2CH_2$— | $SCH_2$(1,1-c-Pr)$CH_2CO_2H$ | $CH_2CH_2$-2-Btz | rac |
| 56 | 7-Cl,H | -1,2-c-Pr— | $SCH_2$(1,1-c-Pr)$CH_2CO_2H$ | $CH_2CH_2$-2-Py | (R) |
| 57 | 6,7-$F_2$ | —CH=CH— | $SCH_2$(1,1-c-Pr)$CH_2CO_2H$ | $CH_2CH_2$-2-Py | (R) |
| 58 | 6,7-$F_2$ | —CH=CH— | $SCH_2$(1,1-c-Pr)$CH_2CO_2H$ | $CH_2CH_2$-2-THQ | (R) |
| 59 | 6,7-$F_2$ | —CH=CH— | $SCH_2$(1,1-c-Pr)$CH_2CO_2H$ | $CH_2CH_2$-2-Fl | (R) |

-continued

| EX. | $R^1, R^1$ | Y | $X^2(CR^3{}_2)mQ$ | $X^3(C(R^3)_2)nZ^2$ | * |
|---|---|---|---|---|---|
| 60 | 6,7-$F_2$ | —CH=CH— | $SCH_2$(1,1-c-Pr)$CH_2CO_2H$ | $CH_2CH_2$-2-(4-i-Pr-Thz) | (R) |
| 61 | 6,7-$F_2$ | —CH=CH— | $SCH_2$(1,1-c-Pr)$CH_2CO_2H$ | $CH_2CH_2$-3-Tl | rac |
| 62 | 7-Cl,H | —CH=CH— | $SCH_2$(1,1-c-Pr)$CH_2CO_2H$ | $CH_2CH_2$-3-(4-Cl-Tl) | rac |
| 63 | 6,7-$F_2$ | —$CH_2CH_2$— | $SCH_2$(1,1-c-Pr)$CH_2CO_2H$ | $CH_2CH_2$-3-Th | rac |
| 64 | 6,7-$F_2$ | —CH=CH— | $SCH_2$(1,1-c-Pr)$CH_2Tz$ | $CH_2CH_2$(2-Br-Ph) | rac |
| 65 | 6,7-$F_2$ | —CH=CH— | $SCH_2$(1,1-c-Pr)$CH_2CONHS(O)_2Me$ | $CH_2CH_2$(2-Cl-Ph) | rac |
| 66 | 6,7-$F_2$ | —CH=CH— | $SCH_2$(1,1-c-Pr)$CH_2CONH$-t-Bu | $CH_2CH_2$(2-F-Ph) | rac |
| 67 | 6,7-$F_2$ | —CH=CH— | $SCH_2$(1,1-c-Pr)$CH_2C(Me)_2OH$ | $CH_2CH_2$(4-SMe-Ph) | rac |
| 68 | 6,7-$F_2$ | —CH=CH— | $SCH_2$(1,1-c-Pr)$CH_2S(O)_2NH_2$ | $CH_2CH_2$(4-$SCF_3$-Ph) | rac |

6. A pharmaceutical composition comprising a therapeutically effective amount of a compound of claim 1 and a pharmaceutically acceptable carrier.

7. A method of preventing the action of leukotrienes in a mammal which comprises administering to said mammal an effective amount of a compound of claim 1.

8. The method of claim 7 wherein the mammal is man.

9. A method of treating asthma in a mammal comprising administering to a mammal in need of such treatment a therapeutically effective amount of a compound of claim 1.

10. The method of claim 9 wherein the mammal is man.

11. A method of treating inflammatory diseases of the eye in mammal which comprises administering to a mammal in need of such treatment a therapeutically effective amount of a compound of claim 1.

* * * * *